US006277982B1

(12) United States Patent
Fraser et al.

(10) Patent No.: US 6,277,982 B1
(45) Date of Patent: Aug. 21, 2001

(54) ALKYLATION OF ALCOHOLS, AMINES, THIOLS AND THEIR DERIVATIVES BY CYCLIC SULFATE INTERMEDIATES

(75) Inventors: Allister S. Fraser; Muthiah Manoharan, both of Carlsbad; Phillip Dan Cook, Fallbrook; Michael E. Jung, Los Angeles; Andrew M. Kawasaki, Carlsbad, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/378,665

(22) Filed: Aug. 20, 1999

(51) Int. Cl.$^7$ .............................. C07H 21/04; C07H 21/00

(52) U.S. Cl. ...................... 536/25.3; 536/23.1; 536/25.31

(58) Field of Search .................................. 536/22.1, 23.1, 536/24.5, 25.3, 25.31, 55.3, 26.26, 27.13, 27.21; 514/44; 435/6, 91.1

(56) References Cited

U.S. PATENT DOCUMENTS

| | | | |
|---|---|---|---|
| 5,138,045 | 8/1992 | Cook et al. | 536/24.5 |
| 5,218,105 | 6/1993 | Cook et al. | 536/25.31 |
| 5,223,618 | 6/1993 | Cook et al. | 544/276 |
| 5,359,044 | 10/1994 | Cook et al. | 536/23.1 |
| 5,378,825 | 1/1995 | Cook et al. | 536/25.34 |
| 5,386,023 | 1/1995 | Sanghvi et al. | 536/25.3 |
| 5,457,191 | 10/1995 | Cook et al. | 536/27.13 |
| 5,459,255 | 10/1995 | Cook et al. | 536/27.13 |
| 5,466,786 | 11/1995 | Buhr et al. | 536/26.26 |
| 5,489,677 | 2/1996 | Sanghvi et al. | 536/22.1 |
| 5,506,351 | 4/1996 | McGee | 536/55.3 |
| 5,541,307 | 7/1996 | Cook et al. | 536/23.1 |
| 5,543,507 | 8/1996 | Cook et al. | 536/23.1 |
| 5,571,902 | 11/1996 | Ravikumar et al. | 536/22.1 |
| 5,578,718 | 11/1996 | Cook et al. | 536/27.21 |
| 5,587,361 | 12/1996 | Cook et al. | 514/44 |
| 5,587,469 | 12/1996 | Cook et al. | 536/23.1 |

FOREIGN PATENT DOCUMENTS

| | | |
|---|---|---|
| 0 322 521 | 7/1989 | (EP) . |
| WO 91/06556 | 5/1991 | (WO) . |
| WO 91/10671 | 7/1991 | (WO) . |
| WO 92/02258 | 2/1992 | (WO) . |
| WO 92/03568 | 3/1992 | (WO) . |
| WO 93/07883 | 4/1993 | (WO) . |
| WO96-06851 * | 3/1996 | (WO) . |
| WO97-45437 * | 12/1997 | (WO) . |
| WO 98/35978 | 8/1998 | (WO) . |

OTHER PUBLICATIONS

Gait, M.J., Oligonucleotide Synthesis: A practical Approach., IRL Press, Oxford, 1984, all pages.*
Ogilvie, K. K., in Nucleoside, Nucleotides an their Biological Applications, Academic Press, New York, 1983.*
Flores et al. Application of Cyclic Sulfates of vic–Diols: Synthesis of Episulfides, Olefins, and Thio Sugars. J. Org. Chem. vol. 62, pp. 3944–3961, Jun. 1997.*
Anderson, K.P., "Antisense Oligonucleotide–Mediated Inhibition of Hepatitis C Virus Gene Expression in Mouse Livers", 2nd International Conference on Therapies for Viral Hepatits, Kona, Hawaii, Dec. 15–19, 1997, 1 page.
Baker, W. et al., "Tetramethylethylene sulphate," *J. Chem. Soc.*, 1961, 2257–2258.
Baker, W. et al., "Cyclic esters of sulphuric acid. Part II. The constitution of methylene and glyoxal sulphates, and the reaction of methylene sulphate with tertiary bases," *J. Chem. Soc.*, 1932, 86–91.
Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells", *J. Biol. Chem.*, 1997, 272, 11994–12000.
Beaucage, S.L., et al., 3H–1,2–Benzodithiole–3one 1,1–Dioxide as an improved sulfurizing reagent in the solid–phase synthesis of oligodeoxyribonucleoside phosphorothioates, *J. Amer. Chem. Soc.*, 1990, 112, 1253.
Beaucage, S.L. et al., "Deoxynucleoside Phosphoramidites–A New Class of Key Intermediates for Deoxypolynucleotide Synthesis", *Tetrahedron Letts.*, 1981, 22, 1859–1862.
Berridge, M.S. et al., "Cyclic sulfated: useful substrates for selective nucleophilic substitution," *J. Org. Chem.*, 1990, 55, 1211–1217.
Bragg, P.D. et al., "The reaction of sulphuryl chloride with clycosides and sugar alcohols, Part I," *Can. J. Chem.*, 1959, 37, 1412–1416.
Brimacombe, J.S. et al., "Aspects of stereochemistry. Part III.. Acidic and basic hydrolysis of some diol cyclic sulphates and related compounds," *J. Chem. Soc.*, 1960, 201–211.
Caruthers, M.H., "Synthesis of Oligonucleotides and Oligonucleotide Analogues", *Oligonucleotides: Antisense Inhibitors of Gene Expression*, 1989, Chapter 1, Cohen, J.S. (ed.), CRC Press, Boca Raton, FL, 7–24.
Caruthers, M.H., "Gene synthesis machines: DNA chemistry and its uses," *Science*, 1985, 281–285.

(List continued on next page.)

Primary Examiner—John L. LeGuyader
Assistant Examiner—Janet Epps
(74) Attorney, Agent, or Firm—Woodcock Washburn Kurtz Mackiewicz & Norris LLP

(57) ABSTRACT

Methods for the alkylation of alcohols, amines and thiols by the use of cyclic sulfates are disclosed. The alkylated sulfates formed are versatile intermediates which may be further elaborated by methods of the invention. In particular, methods for the alkylation of the 2', 3' or 5'-hydroxy position of nucleosides and nucleoside analogs with cyclic sulfates to form the 2', 3' or 5'-O-alkyl sulfate modified compounds are disclosed. Displacement of the 2',3' or 5'-O-sulfate with a nucleophile provides 2', 3' or 5'-O-modified nucleosides and nucleoside analogs useful for the synthesis of oligomeric compounds having improved hybridization affinity and nuclease resistance.

62 Claims, 13 Drawing Sheets

OTHER PUBLICATIONS

Chladek, S. et al., "Oligonucleotidic compounds v.* 2',3'–o–alkylidene derivatives of ribonucleosides," *Coll. Czech. Chem.*, 1963, 28, 1301–1308.

Cook, P.D., "Second Generation Antisense Oligonucleotides: 2'–Modifications", Bristol, J.A. (ed.), *Annu. Rep. Med. Chem.*, Academic Press, New York, 1998, 33, 313–325.

Cowsert, L. M. et al., "In vitro and In Vivo Activity of Antisense Inhibitors of ras: Potential for Clinical Development," *Anti–Cancer Drug Design*, 1997, 12, 359–371.

Cramer, F. et al., "Über substituierte 2.3–benzyliden–ribonucleoside," *Ann. Der Chemie*, 1964, 679, 156–163.

Crooke, S.T. et al., "Pharmacokinetic Properties of Several Novel Oligonucleotide Analogs in mice", *J. Pharmacol. Exp. Therapeutics*, 1996, 277, 923–937.

Denmark, S.E., "Facile oxetane formation in a rigid bicyclo [2.2.2]octane system," *J. Org. Chem.*, 1981, 46, 3144–3147.

Gao, Y. et al., "Vicinal diol cyclic sulfates: like epoxides only more reactive," *J. Am. Chem. Soc.*, 1988, 110, 7538–7539.

Garner, H.K. et al., "Preparation and hydrolysis of some acetals and esters of D(–)–2,3–butanediol," *J. Am. Chem. Soc.*, 1950, 72, 5497–5501.

Gioeli, C. et al., "The tetraisopropyldisiloxane–1,3–DIYL: a versatile protecting group for the synthesis of adenylyl–(2'→5')–adenosine (2–5A core)," *Tetrahedron Lett.*, 1981, 22, 1741–1744.

Goren, M.B. et al., "The stringent requirement for electrophiles in the facile solvolytic hydrolysis of neutral sulfate ester salts," *J. Org. Chem.*, 1973, 38, 3510–3513.

Guschlbauer et al., "Nucleoside conformation is determined by the electronegativity of the sugar substituent", *Nucl. Acids Res.*, 1980, 8(6), 1421–1433.

Hampton, A. et al., "Nucleotides. IV. Conversion of ribonucleosides to new 2',3'–ketal derivatives," *J. Am. Chem. Soc.*, 1965, 87, 5481–5487.

Hampton, A., "Nucleotides. II. A new procedure for the conversion of ribonucleosides to 2',3'–O–isopropylidene derivatives," *J. Am. Chem. Soc.*, 1961, 83, 3640–3645.

Hanecak, R. et al., "Antisense Oligonucleotide Inhibition of Hepatitis–C Virus Gene Expression in Transformed Hepatocytes," *Jour. Virology*, 1996, 70(8), 5203–5212.

Hobbs, J. et al., "Polynucleotides Containing 2'–Chloro–2'–deoxyribose", *Biochem.*, 1972, 11, 4336–4344.

Ikehara, M. et al., "Polynucleotides. LVI. Synthesis and properties of poly(2'–deoxy–2'–fluroadenylic acid)", *Nucl. Acids Res.*, 1978, 5, 3315–3325.

Ikehara, M. et al., "Polynucleotides. L. Synthesis and properties of poly(2'–chloro–2'–deoxyadenylic acid) and poly(2'–bromo–2'–deoxyadenylic acid)", *Nucl. Acids Res.*, 1977, 4, 4249–4260.

Iyer, R.P., et al., "3H–1,2–Benzodithiole–3–one 1,1–dioxide as an improved sulfurizing reagent in the solid–phase synthesis of oligodeoxyribonucleoside phosphorothioate," *J. Am. Chem. Soc.*, 1990, 112, 1253–1254.

Inoue, H. et al., "Synthesis and hybridization studies on two complementary nona(2'–O–methyl)ribonucleotides", *Nucl. Acids Res.*, 1987, 15, 6131–6148.

Jarman, M. et al., "Ribonucleoside 2',3'–cyclic orthoformates," *Chem. Ind. (London)*, 1964, 1493–1494.

Jones, S.S. et al., "Migration of t–butyldimethylsilyl protecting groups," *J. Chem. Soc. Perkins Trans.*, 1979, 1, 2762–2764.

Jones, J.K.N. et al., "The reaction of sulphuryl chloride with glycosides and sugar alcohols. Part II," *Can. J. Chem.*, 1960, 38, 1122–1129.

Kawasaki et al., "Synthesis, Hybridization, and Nuclease Resistance Properties of 2'–O–Aminooxyethyl Modified Oligonucleotides", Gosselin, G. et al. (eds.), *XIII International Round Table, Nucleosides, Nucleotides, and their Biological Applications*, Montpellier, France, Sep. 6–10, 1998, 16 pages.

Kim, B.M. et al., "A short route to β–lactams: use of cyclic sulfites from syn–2,3–dihydroxy esters," *Tetrahedron Lett.*, 1990, 31(30), 4317–4320.

Kim, B.M. et al., "Cyclic sulfates containing acid–sensitive groups and chemoselective hydrolysis of sulfate esters," *Tetrahedron Lett.*, 1989, 30(6), 655–658.

Lichtenberger, J. et al., "No. 230.—Sur les sulfates de diols (4' mémoire)," *Bull. Soc. Chim. Fr.*, 1961, 1495–1498.

Lohray, B.B. et al., "Synthesis of homochiral amino alcohols, aziridines and diamines via homochiral cyclic sulphites," *J. Chem. Soc., Chem. Commun.*, 1991, 95–97.

Lohray, B.B., "Cyclic sulfites and cyclic sulfates: epoxide like synthons," *Synthesis*, 1992, 11, 1035–1394.

Lowe, G. et al., "Application of a lanthanide shift reagent in $^{17}$O N. M.R. spectroscopy to determine the stereochemical course of oxidation of cyclic sulphite diesters to cyclic sulphate diesters with ruthenium tetroxide," *J. Chem. Soc., Chem. Commun.*, 1983, 1392–1394.

Lowe, G. et al., "Synthesis and configurational assignment of some novel bicyclic sulphamidites and sulphamidates," *Tetrahedron Asymmetry*, 1990, 1(12), 885–894.

Lowe, G. et al., "Enantiomeric chiral [$^{16}$O, $^{17}$O, $^{18}$O] sulphate esters," *J. Chem. Soc., Chem. Commun.*, 1984, 466.

Lowe, G. et al., "The crystal structure of some 2–Oxo–1,3, 2–dioxathiolanes," *J. Chem. Soc., Chem. Commun.*, 1984, 262–264.

Machinga, N. et al., "Enantiodivergent total synthesis of naturally occurring trans–2–BUTYL–5–Pentylpyrrolidine," *Tetrahedron Lett.*, 1990, 31(25), 3637–3640.

Manoharan, M. et al., "Novel Functionalization of the Sugar Moiety of Nucleic Acids for Multiple Labeling in the Minor Groove", *Tetrahedron Letts.*, 1991, 32, 7171–7174.

Markiewicz, W.T. et al., "A new type of silyl protecting groups in nucleoside chemistry," *Nucleic Acids Res. Spec. Publ.*, 1978, s185–s188.

Martin, P., "Ein neuer Zugang zu 2'–O–Alkylribonucleodsiden und Eigenschaften deren Oligonucleotide", *Helvetica Chemica Acta*, 1995, 78, 486–504 (English summary included).

Monia, B.P. et al., "Evaluation of 2'–Modified Oligonucleotides Containing 2'–Deoxy Gaps as Antisense Inhibitors of Gene Expression", *J. Biol. Chem.*, 1993, 268, 14514–14522.

Nishinaga, A. et al., "Cyclic sulfate formation from epoxides," *Chem. Lett.*, 1978, 913–914.

Noda, Y., "A new imino acid derived from $_L$–serine O–sulfate," *Bull. Chem. Soc. Jpn.*, 1967, 40(6), 1554.

Ohtsuka, E. et al., "Recognition by restriction endonuclease EcoRI of deoxyoctanucleotides containing modified sugar moieties", *J. Biochem.*, 1984, 139, 447–450.

Pankiewicz, K.W. et al., "Nucleosides. 130. Synthesis of 2'–deoxy–2'–substituted– and 5'–deoxy–5'–substituted– uridine derivatives. Crystalline and molecular structure of 2'–chloro–2'–deoxy–1,3–dimethyl– –uridine. Studies directed toward the synthesis of 2'–deoxy–2'–substituted–arabino–nucleosides. 1[1]," *Heterocycl. Chem.*, 1985, 22, 1703–1710.

Pankiewicz, K.W. et al., "Nucleosides. 125, Synthesis of 5'–substituted–1,3–dimethyl–uridines from 3',5'–O–(1,1,3,3–tetraisopropyldisiloxanyl)–1,3–dimethyl– –uridine. A novel isomerization reaction," *J Nucleic Acids Res. Symp. Ser.*, 1982, 11, 9–12.

Peoc'h et al., "Synthesis and Evaluation of 2'–Modified MMI Linked Dimers in Antisense Constructs", *Nucleosides Nucleotides*, 1997, 16(7–9), 959–962.

Pierre, R., et al., "Process for the preparation of cyclic sulfates," *Chem. Abstr.*, 1990, 112, 77201, p. 805.

Poorker, C.S. et al., "The facile addition of fluorosulfuric acid to an epoxide," *Tetrahedron Lett.*, 1985, 26(52), 6405–6408.

Pritchard, J.G. et al., "Proton magnetic resonance, structure and stereoisomerism in cyclic sulfites," *J. Am. Chem. Soc.*, 1961, 83, 2105–2110.

Reese, C.B. et al., "Monoacylation of ribonucleoside derivatives via orthoester exchange," *Proc. Chem. Soc.*, 1964, 214–215.

Reibere, F. et al., "An efficient route to chiral t–butyl sulfoxides," *Tetrahedron Lett.*, 1989, 30(28), 3659–3662.

Robertson, F.M. et al., "Production and properties of 2,3–butanediol," *Can. J. Res.* 1947, 25(B), 491–493.

Robins, M.J. et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.*, 1983, 105, 4059–4065.

Secrist, J.A. et al., "Synthesis and Biological Activity of 4'Thionucleosides", *10th International Roundtable: Nucleosides, Nucleotides and their Biological Applications*, Sep. 16–20 1992, Abstract 21, Park City, Utah, 40.

Sheehan, J.C. et al., "Sulfonation of unsaturated compounds. I. Sulfonation of branched–chain ketones with sulfur trioxide. A one–step synthesis of tetramethylene sulfate through a retro pinacol–type rearrangement," *J. Org. Chem.*, 1974, 39, 3415–3416.

Shibahara, S. et al., "Inhibition of human immunodeficiency virus (HIV–1) replication by synthetic oligo–RNA derivatives", *Nucl. Acids Res.*, 1989, 17, 239–252.

Smith, M. et al., Studies on Polynucleotide. XIV. Specific Synthesis of the C3–C5 Interribonucleotide Linkage. Syntheses of Uridylyl– (3'–5')–Uridine and Uridylyl–(3'–5')–Adenosine2, *J. Am. Chem. Soc.*, Feb. 5, 1962, 84, 430–440.

Tabushi, I. et al., "Sulfuryl chloride," in *Synthetic Reagents*, Pizey, J.S. (ed.), Ellis Horwood, Chichester, 1981, vol. 4, Chap. 3, 336–396.

Takaku, H. et al., "Synthesis of Oligoribonucleotides Using 4–Methoxybenzyl Group as a New Protecting Group of the 2'–Hydroxyl Group of Adenosine", *Chem. Letts.*, 1982, 189–192.

Takano, S. et al., "Preparation of chiral fluorine compounds from (2s, 3s)–3–Phenylglycidol," *Chem. Lett.*, 1989, 1689–1690.

Tewson, T.J. et al., "1–propenyl 4,6–O–Benzylidine–β–D–Mannopyranoside–2,3–cyclic sulfate: A substrate for the synthesis of [F–18] 2–deoxy–2–fluoro–D–glucose," *J., Carbohydr. Chem.*, 1985, 4(4), 529–543.

Tewson, T.J., "Cyclic sulfur esters as substrates for nucleophilic substitution. A new synthesis of 2–deoxy–2–fluoro–D–glucose," *J. Org. Chem.*, 1983, 48, 3507–3510.

Tillett, J.G., "Reactivity of sulfur heterocycles," *Phosphorous Sulfur*, 1976, 1, 341–349.

Tomalia, D.A. et al., "The synthesis and reactions of β–substituted ethyl sufates," *J. Heterocycl. Chem.*, 1972, 9, 891–894.

Van der Klein, P.A.M. et al., Iodonium ion promoted cyclization: a convenient approach to glycosyl donors of 3–deoxy–D–manno–2–octulosonic acid (KDO), *Synlett*, 1990, 311–313.

Van der Klein, P.A.M. et al., "An efficient route to 3–deoxy–D–manno–2–Octulosonic acid (DKO) derivatives via a 1,4–cyclic sulfate approach," *Tetrahedron Lett.*, 1989, 30(40), 5477–5480.

Vanessche, K. et al., "L–ribulose: a novel chiral pool compound," *Tetrahedron Lett.*, 1990, 31(16), 2337–2340.

Walker et al., "Analysis of Hydroxylamine Glycosidic Linages: Structural Consequences of the NO Bond in Calicheamicin", *J. Am. Chem.*, 1994, 116, 3197–3206.

Zemlicka, J., "2',3'–0–alkoxymethylene derivatives of ribonucleosides," *Chem. Ind.(London)*, 1964, 581.

IRL Press, Oxford, (1984) Gait, M.J., Oligonucleotide Synthesis: APractical Approach.

\* cited by examiner

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage
<221> NAME/KEY: misc_feature
<222> LOCATION: (2)
<223> OTHER INFORMATION: 5-methyl-C
<221> NAME/KEY: misc_feature
<222> LOCATION: (10)
<223> OTHER INFORMATION: 5-methyl-C
<221> NAME/KEY: misc_feature
<222> LOCATION: (18)
<223> OTHER INFORMATION: 5-methyl-C

<400> SEQUENCE: 1
tctgagtagc agaggagctc                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: Description of Artificial Sequence: Novel
      Sequence
<221> NAME/KEY: misc_feature
<222> LOCATION: (1)..(19)
<223> OTHER INFORMATION: a phosphodiester linkage
<221> NAME/KEY: misc_feature
<222> LOCATION: (2)
<223> OTHER INFORMATION: 5-methyl-C
<221> NAME/KEY: misc_feature
<222> LOCATION: (10)
<223> OTHER INFORMATION: 5-methyl-C
<221> NAME/KEY: misc_feature
<222> LOCATION: (18)
<223> OTHER INFORMATION: 5-methyl-C

<400> SEQUENCE: 2
tctgagtagc agaggagctc                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage
<221> NAME/KEY: misc_feature
<222> LOCATION: (4)
<223> OTHER INFORMATION: 5-methyl-C
<221> NAME/KEY: misc_feature
<222> LOCATION: (8)
<223> OTHER INFORMATION: 5-methyl-C
<221> NAME/KEY: misc_feature
<222> LOCATION: (11)..(15)
<223> OTHER INFORMATION: 5-methyl-C

<400> SEQUENCE: 3
atgcattctg cccccaagga                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage
<221> NAME/KEY: misc_feature
<222> LOCATION: (2)..(4)
<223> OTHER INFORMATION: 5-methyl-C
<221> NAME/KEY: misc_feature
<222> LOCATION: (8)
<223> OTHER INFORMATION: 5-mehtyl-C
<221> NAME/KEY: misc_feature
<222> LOCATION: (12)
<223> OTHER INFORMATION: 5-methyl-C
<221> NAME/KEY: misc_feature
<222> LOCATION: (15)..(16)
<223> OTHER INFORMATION: 5-methyl-C
<221> NAME/KEY: misc_feature
<222> LOCATION: (19)
<223> OTHER INFORMATION: 5-methyl-C

<400> SEQUENCE: 4
gcccaagctg gcatccgtca                                                   20

<210> SEQ ID NO 5
<211> LENGTH: 19
<212> TYPE: DNA
```

```
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (16)..(19)
<223> OTHER INFORMATION: 2'-modified T

<400> SEQUENCE: 5
tttttttttt tttttttt                                                   19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage

<400> SEQUENCE: 6
tccgtcatcg ctcctcaggg                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage

<400> SEQUENCE: 7
tcagtaatag gcccacatgg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(3)
<223> OTHER INFORMATION: a phosphodiester linkage
<221> NAME/KEY: misc_feature
<222> LOCATION: (4)..(12)
<223> OTHER INFORMATION: a phosphorothioate linkage
<221> NAME/KEY: misc_feature
<222> LOCATION: (13)..(19)
<223> OTHER INFORMATION: a phosphodiester linkage

<400> SEQUENCE: 8
ttcgtcatcg ctcctcaggg                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage

<400> SEQUENCE: 9
```
tccgtcatcg ctcctcaggg                                              20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(3)
<223> OTHER INFORMATION: a phosphodiester linkage
<221> NAME/KEY: misc_feature
<222> LOCATION: (4)..(16)
<223> OTHER INFORMATION: a phosphorothioate linkage
<221> NAME/KEY: misc_feature
<222> LOCATION: (17)..(25)
<223> OTHER INFORMATION: a phosphodiester linkage

<400> SEQUENCE: 10
tcagtaatag ccgccgcccc acatgg                                       26

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(22)
<223> OTHER INFORMATION: a phosphorothioate linkage

<400> SEQUENCE: 11
tcagtaatag ccgccccaca tgc                                          23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(19)
<223> OTHER INFORMATION: a phosphorothioate linkage

<400> SEQUENCE: 12
tccgtcatcg ctcctcaggg                                              20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(22)
<223> OTHER INFORMATION: a phosphorothioate linkage

<400> SEQUENCE: 13
tcagtaatag ccgccccaca tgc                                          23

<210> SEQ ID NO 14
<211> LENGTH: 20
<212> TYPE: DNA
<213> ORGANISM: Artificial Sequence
<220> FEATURE:

<223> OTHER INFORMATION: Description of Artificial Sequence: Novel
      Sequence
<221> NAME/KEY: misc_feature
<222> LOCATION: (1)..(20)
<223> OTHER INFORMATION: 2'deoxy

<400> SEQUENCE: 14
tttaggattc gtgctcatgg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(20)
<223> OTHER INFORMATION: 2'-MOE

<400> SEQUENCE: 15
tttaggattc gtgctcatgg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(20)
<223> OTHER INFORMATION: 2'-O-DMAP

<400> SEQUENCE: 16
tttaggattc gtgctcatgg                                              20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
atgcattctg ccccaagga                                               19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(4)
<223> OTHER INFORMATION: a phosphodiester linkage
<221> NAME/KEY: misc_feature
<222> LOCATION: (5)..(14)
<223> OTHER INFORMATION: a phosphorothioate linkage
<221> NAME/KEY: misc_feature
<222> LOCATION: (15)..(18)
<223> OTHER INFORMATION: a phosphodiester linkage

<400> SEQUENCE: 18
atgcattctg ccccaagga                                               19

<210> SEQ ID NO 19

```
<211> LENGTH: 19
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(18)
<223> OTHER INFORMATION: a phosphorothioate linkage

<400> SEQUENCE: 19
atgcattctg ccccaagga                                                   19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(4)
<223> OTHER INFORMATION: a phosphodiester linkage
<221> NAME/KEY: misc_feature
<222> LOCATION: (5)..(14)
<223> OTHER INFORMATION: a phosphorothioate linkage
<221> NAME/KEY: misc_feature
<222> LOCATION: (15)..(18)
<223> OTHER INFORMATION: a phosphodiester linkage

<400> SEQUENCE: 20
atgcattctg ccccaagga                                                   19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)..(18)
<223> OTHER INFORMATION: a phosphorothioate linkage

<400> SEQUENCE: 21
atgcattctg ccccaagga                                                   19

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (1)
<223> OTHER INFORMATION: 2'-O-[3-(N,N-dimethyl)aminopropyl]5-methyl-U
<221> NAME/KEY: misc_feature
<222> LOCATION: (7)
<223> OTHER INFORMATION: 2'-O-[3-(N,N-dimethyl)aminopropyl]5-methyl-U
<221> NAME/KEY: misc_feature
<222> LOCATION: (9)
<223> OTHER INFORMATION: 2'-O-[3-(N,N-diemthyl)]5-methyl-U
<221> NAME/KEY: misc_feature
<222> LOCATION: (15)
<223> OTHER INFORMATION: 2'-O-[3-N,N-dimethyl)aminopropyl]5-methyl-U

<400> SEQUENCE: 22
tccaggtgtc cgcatc                                                      16

<210> SEQ ID NO 23
```

```
<211> LENGTH: 18
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (8)..(11)
<223> OTHER INFORMATION: 2'-O-[3-(N,N-dimethyl)aminopropyl]5-methyl-U

<400> SEQUENCE: 23 ctcgtactttt tccggtcc                                                        18

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (4)..(13)
<223> OTHER INFORMATION: 2'-O-[3-(N,N-dimethyl)aminopropyl]5-methyl-U

<400> SEQUENCE: 24
gcgttttttt tttgcg                                                           16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 25
tccaggtgtc cgcatc                                                           16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 26
gcgttttttt tttgcg                                                           16

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 27 ctcgtactttt tccggtcc                                                        18
```

ALKYLATION OF ALCOHOLS, AMINES, THIOLS AND THEIR DERIVATIVES BY CYCLIC SULFATE INTERMEDIATES

FIELD OF THE INVENTION

This invention is directed to methods of alkylation of alcohols, amines, thiols and their derivatives by cyclic sulfate intermediates. In particular, the invention is directed to the alkylation of pentosyl sugar moieties at the 2',3' or 5'-hydroxyl positions. These methods are especially useful for the preparation of 2'-O-alkyl nucleotides, nucleosides and nucleoside surrogates that are precursors for the preparation of oligomeric compounds. Such oligomeric compounds are beneficial as therapeutics, diagnostics, and research reagents.

BACKGROUND OF THE INVENTION

It has been recognized that oligonucleotides and oligonucleotide analogs (oligomeric compounds) can be used to modulate mRNA expression by a mechanism that involves the complementary hybridization of relatively short oligonucleotides to mRNA such that the normal and essential functions of these intracellular nucleic acids are disrupted. Hybridization is the sequence-specific base pair hydrogen bonding of an oligonucleotide to a complementary RNA or DNA.

Oligonucleotides are used as diagnostics, therapeutics and as research reagents. For this, the ability of an oligonucleotide to bind to a specific DNA or RNA with fidelity is an important factor. The relative ability of an oligonucleotide to bind to complementary nucleic acids is compared by determining the melting temperature of a particular hybridization complex. The melting temperature ($T_m$), a characteristic physical property of double helices, is the temperature (in °C.) at which 50% helical versus coil (unhybridized) forms are present. $T_m$ is measured by using UV spectroscopy to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the $T_m$, the greater the strength of the binding of the nucleic acid strands. Therefore, oligonucleotides modified to hybridize with appropriate strength and fidelity to targeted RNA (or DNA) are greatly desired for use as research reagents, diagnostic agents, and as oligonucleotide therapeutics.

Various modifications to the base, sugar and internucleoside linkage have been introduced into oligonucleotides at selected positions, and the resultant effect relative to the unmodified oligonucleotide compared. A number of modifications have been shown to improve one or more aspects of the oligonucleotide. Useful 2'-modifications that have been shown to improve aspects of oligonucleotides include halo, alkoxy and allyloxy groups. Many 2'-O-modified oligonucleotides having increased hybridization and nuclease resistance have been used in antisense research.

The use of antisense compounds as drug candidates with potential clinical applications requires that they form stable duplexes with target mRNA's, prevent translation of messages (most often via RNase H-mediated cleavage), and have resistance to nucleases. Phosphorothioate backbone modified oligonucleotides having 2'-O-modified monomers at selected positions have been reported to be effective antisense molecules (Cook, P. D., Second Generation 2'-Modified Antisense Oligonucleotides, J. A. Bristol (Ed.), *Annu. Rep. Med. Chem.*, 1998, 33, 313, Academic Press, New York). The phosphorothioate internucleoside linkage enhances nuclease resistance, while the 2'-O-modification increases hybridization. Superior antisense activity has been shown for 2'-O-modified oligomeric compounds (Martin et al., *Helv. Chim. Acta.*, 1995, 78, 486). These oligonucleotides were prepared using "gapmer" technology (Monia et al., *J. Biol. Chem.*, 1993, 268, 14514). Gapmer technology utilizes nuclease-resistant internucleoside linkages at selected positions while using native or other internucleoside linkages at internal positions. Generally, the 3' and 5' regions of the oligomeric compound will have contiguous internucleoside linkages providing superior nuclease resistance while the internal region may have native or other internucleoside linkages.

In addition to 2'-O-methoxyethyl modified oligomeric compounds, oligomeric compounds having pseudoisosteres of 2'-O-methoxyethyl modification have also shown superior hybridization qualities. Included in this group of 2'-O-modifications is the 2'-O-aminooxyethyl (AOE) modification (Kawasaki et al., Synthesis, Hybridization, and Nuclease Resistance Properties of 2'-O-Aminooxyethyl Modified Oligonucleotides, G. Gosselin and B. Rayner (Eds.), *XIII International Round Table, Nucleosides, Nucleotides, and their Biological Applications*, 1998, Montpellier, France). The hydroxylamino function present in this modification is observed in nature in the form of glycosylated antibiotics (Walker et al., *J. Am. Chem. Soc.*, 1994, 116, 3197). The hydroxylamino function has also been synthetically incorporated into oligonucleotide backbones (Peoc'h et al., *Nucleosides Nucleotides*, 1997, 16, 959). Among the unique properties of the hydroxylamino function are the unusual conformational preferences of the N—O bond and the surprisingly low $pK_a$ (MeONH$_2$, 4.2, MeONHMe, 4.75, MeONHMe$_2$, 3.65).

The inclusion of one or more 2'-O-(aminooxyethyl) moieties in an oligonucleotide provides, inter alia, improved binding of the oligonucleotide to a complementary strand. The inclusion of one or more 2'-O-(aminooxyethyl) moieties in an oligomeric compound also provides one or more sites useful for the conjugation of various useful ligands. Such ligands include, for example, reporter groups and groups for modifying uptake, distribution or other pharmacodynamic properties.

Ikehara has reported the synthesis of a mixed octamer containing one 2'-deoxy-2'-fluoroguanosine residue or one 2'-deoxy-2'-fluoroadenine residue (Ikehara et al., *European J. Biochem.*, 1984, 139, 447). Guschlbauer and Jankowski have shown that the contribution of the C-3'-endo conformer increases with increasing electronegativity of the 2'-substituent (*Nucleic Acids Res.*, 1980, 8, 1421). Thus, 2'-deoxy-2'-fluorouridine contains 85% of the C-3'-endo conformer.

Furthermore, evidence has been presented which indicates that 2'-substituted-2'-deoxyadenosine polynucleotides resemble double-stranded RNA rather than DNA (Ikehara et al., *Nucleic Acids Res.*, 1978,5,3315). Ikehara has also shown that a2'-fluoro substituent in poly A, poly I, or poly C duplexed to its complement is significantly more stable than the ribonucleotide or deoxyribonucleotide poly duplex as determined by standard melting assays (Ikehara et al, *Nucleic Acids Res.*, 1978, 4, 4249). Eckstein has shown that a 2'-chloro or 2'-bromo substituent in poly (2'-deoxyadenylic acid) provides nuclease resistance (Eckstein et al., *Biochemistry*, 1972, 11, 4336). Inoue has reported that poly(2'-chloro-2'-deoxy-uridylic acid) and poly (2'-chloro-2'-deoxycytidylic acid) are resistant to various nucleases and have described the synthesis of mixed oligonucleotide sequences containing 2'-OMe substituents on every nucleotide (Inoue et al., *Nucleic Acids Res.*, 1987, 15, 6131). The mixed 2'-OMe-substituted oligonucleotide hybridized to its RNA complement as strongly as the RNA-RNA duplex which is significantly stronger than the same sequence RNA-DNA hetero duplex ($T_m$s, 49.0 and 50.1 versus 33.0 degrees for nonamers). Shibahara has reported the synthesis of mixed oligonucleotides containing 2'-OMe substituents on every nucleotide. The mixed 2'-OMe-substituted oligonucleotides were designed to inhibit HIV replication (Shibahara et al., *Nucleic Acids Res.*, 1987, 17, 239).

While not wishing to be bound, it is believed that the composite effect of the hydroxyl group's steric effect, its hydrogen bonding capabilities, and its electronegativity versus the properties of the hydrogen atom is responsible for the gross structural difference between RNA and DNA. Thermal melting studies indicate that the order of duplex stability (hybridization) of 2'-methoxy oligonucleotides is in the order of RNA-RNA>RNA-DNA>DNA-DNA.

International Publication Number WO 91/06556, published May 16, 1991, and U.S. Pat. No. 5,466,786 disclose oligomers derivatized at the 2'-position with substituents. These oligomers are stable to nuclease activity. Specific 2'-O-substituents which were incorporated into oligonucleotides include ethoxycarbonyl-methyl (ester form), and its acid, amide and substituted amide forms.

Martin has disclosed certain nucleosides, and oligonucleotides prepared therefrom, that include 2'-methoxyethoxy, 2'-methoxy(tris-ethoxy) and other substituents. Oligonucleotides containing nucleosides substituted with either the 2'-methoxyethoxy and 2'-methoxy (tris-ethoxy) substituents exhibited improved hybridization, as judged by increase in $T_m$ (Martin, et. al., *Helvetica Chimica Acta*, 1995, 78, 486).

It has been recognized that oligomeric compounds having improved hybridization and nuclease resistance are of great importance in the development of useful research reagents, diagnostic agents and therapeutic agents. For the foregoing reasons, there exists a need in the art for improved processes, especially for the preparation of 2'-O-modified nucleosidic oligomeric compounds, which are more facile, are faster and are cheaper than processes currently known in the art.

BRIEF DESCRIPTION OF THE DRAWINGS

The drawings presented herewith and the attendant examples are not to be construed as limited the invention in any way, but rather as serving only for purposes of exemplification.

FIG. 5 3'-hydroxyl alkylation of 5'-O-DMT-2'-O-[2-(N,N-dimethyl)aminopropyl]-5-methyluridine 7 with succinic anhydride and attachment of 5'-O-DMT-2'-O-[3-(N,N-dimethyl) aminopropyl]-3'-O-succinyl-5-methyluridine 9 to CPG.

FIG. 8 3'-hydroxyl alkylation of 5'-O-DMT-2'-O-[2-(thiomethyl)ethyl]-5-methyluridine 13 with succinic anhydride and attachment of 5'-O-DMT-2'-O-[2-(thiomethyl) ethyl]-3'-O-succinyl-5-methyluridine 15 to CPG.

SUMMARY OF THE INVENTION

Figure 1:
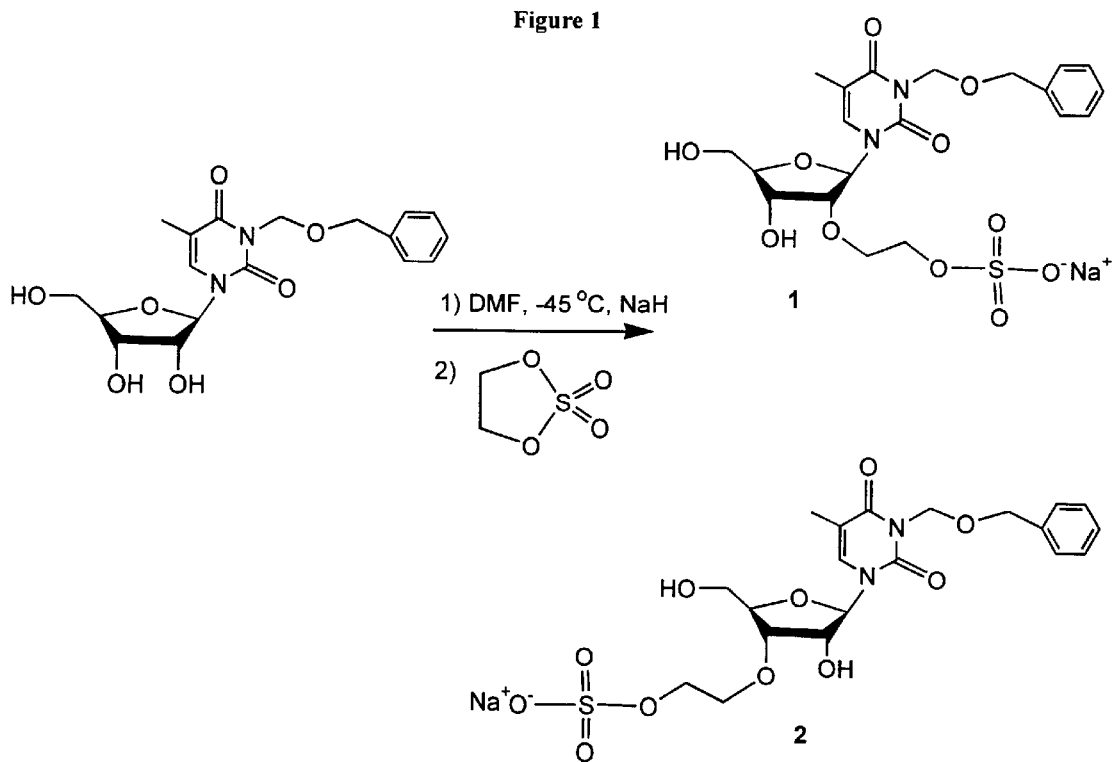
FIG. 1 Alkylation of N-3-(benzyloxy)methyl-5-methyluridine with 1,3,2-dioxathiolane 2,2-dioxide.

The present invention provides methods for the alkylation of alcohols, amines and thiols that use cyclic sulfates as reactive alkylating agents. These cyclic sulfates undergo ring opening in the presence of a nucleophile. The alkylated intermediate sulfates may be further elaborated by a further nucleophilic displacement of the sulfate. In particular, the 2', 3' and 5'-hydroxyl position of a pentosyl sugar moiety may be alkylated. These methods are especially useful for the synthesis of 2'-O-alkyl nucleosides, which in turn serve as precursors in the preparation of oligomeric compounds.

In an embodiment of the invention, nucleosides bearing protected and unprotected 240 , 3' and 5'-hydroxyl functionalities are treated with a base and alkylated with a cyclic sulfate to form O-alkyl sulfate nucleosides. Displacement of the sulfate intermediate with a nucleophile affords an O-modified nucleoside. In another embodiment of the invention, acid hydrolysis of the product sulfate gives an alcohol which may be used as an intermediate for subsequent nucleoside modification.

An embodiment of the invention provides methods for the preparation of a compound of formula I;

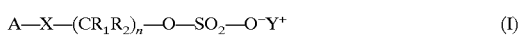

wherein:

A is a carbohydrate, an oligonucleotide, a nucleotide, or a nucleoside;

X is a O, S, or N;

$R_1$ and $R_2$ are independently H, alkyl, aryl, O-alkyl, O-aryl, carboxylic acid, amide, ester, halogen, trifluoro-methyl, or amine;

n is 2–10; and,

Y is H,Li,Na,K,Cs or an amine.

The method preferably comprises the steps of:

selecting or providing a compound having formula II;

  (II)

wherein:

X is a O, S, or N; and, treating or reacting the compound of formula II with a compound having formula III,

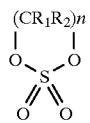

wherein:

$R_1$ and $R_2$ are independently H, alkyl, aryl, O-alkyl, O-aryl, carboxylic acid, amide, ester, halogen, trifluoro-methyl, or amine; and, n is 2–10.

The foregoing reaction or treatment gives rise to the desired compound of formula I.

In a preferred embodiment of the invention, A is a purine or a pyrimidine β-D-ribofuranosyl nucleoside or a purine or a pyrimidine β-D-2'-deoxyribofuranosyl nucleoside. In another preferred embodiment, the treating step includes reacting the compound of formula II in a solution, especially one which is comprised of an aprotic solvent such as acetonitrile, dimethylacetamide, dimethylformamide, dimethylsulfoxide or tetrahydrofuran.

The solution is conveniently and preferably cooled from about 0° C. to about –78° C. and treated with a base. The base is preferably a metal hydride, hydroxide or carbonate such as the exemplary sodium hydride, potassium hydride, lithium hydride, sodium hydroxide, potassium hydroxide, lithium hydroxide, sodium carbonate, potassium carbonate or cesium carbonate. An preferred embodiment uses sodium hydride as the base.

The solution is preferably warmed after addition of the base from about –78° C. to about 0° C. during a period of from about 5 minutes to about 60 minutes and then cooled again from about 0° C. to about –78° C. The solution is then treated with a cyclic sulfate optionally, but preferably one which is substituted with alkyl, aryl, O-alkyl, O-aryl, carboxylic acid, amide, ester, halogen, trifluoromethyl or amine. In another preferred embodiment the solution is treated with an optionally substituted 5- or 6-membered ring cyclic sulfate. It is preferred that the resulting solution be warmed from about 0° C. to about 20° C. from about 1 hour to about 24 hours to ensure complete reaction.

The invention also provides methods for preparing compounds of formula IV;

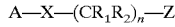  (IV)

wherein:

A is a carbohydrate, an oligonucleotide, a nucleotide, or a nucleoside;

X is a O, S, or N;

$R_1$ and $R_2$ are independently H, alkyl, aryl, O-alkyl, O-aryl, carboxylic acid, amide, ester, halogen, trifluoromethyl, or amine;

n is 2–10; and,

Z is H, amine, azide, halogen, thiol, O-alkyl, O-aryl, alkyl, or aryl.

Such methods may comprise the steps of:

selecting a compound of formula II,

  (II)

wherein:

X is a O, S, or N; and, treating said compound of the formula II with a compound of Formula III,

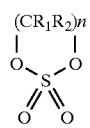

wherein:

$R_1$ and $R_2$ are independently H, alkyl, aryl, O-alkyl, O-aryl, carboxylic acid, amide, ester, halogen, trifluoromethyl, or amine; and, n is 2–10.

This gives an intermediate of the following formula:

wherein:

A is a carbohydrate, an oligonucleotide, a nucleotide, or a nucleoside;

X is a O, S, or N;

$R_1$ and $R_2$ are independently H, alkyl, aryl, O-alkyl, O-aryl, carboxylic acid, amide, ester, halogen, trifluoromethyl, or amine;

n is 2–10; and

Y is H,Li,Na,K,Cs or an amine.

This compound is then reacted with a nucleophile to give the compound of formula IV. In a preferred embodiment of the invention, the intermediate compound is reacted with a nucleophile at a temperature of from about 0° C. to about 200° C. for from about 1 hour to about 24 hours. The nucleophile is preferably an amine such as the exemplary dimethylamine. In another embodiment, the nucleophile is an alkoxide such as sodium methoxide or similar materials. In certain preferred embodiments, the nucleophile is a thiol such as the preferred sodium thiomethoxide. The nucleophile may also be a diester of a malonic acid or similar species.

Another embodiment of the invention is directed to compounds of formula:

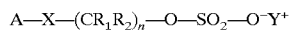

wherein:

A is a carbohydrate, an oligonucleotide, a nucleotide, or a nucleoside;

X is a O, S, or N;

$R_1$ and $R_2$ are independently H, alkyl, aryl, O-alkyl, O-aryl, carboxylic acid, amide, ester, halogen, trifluoro-methyl, or amine;

n is 2–10; and,

Y is H,Li,Na,K,Cs or an amine.

A may advantageously be a purine or a pyrimidine β-D-ribofuranosyl nucleoside or a purine or a pyrimidine β-D-2'-deoxyribofuranosyl nucleoside.

Another preferred embodiment of the invention provides methods for preparing compounds of the formula VI;

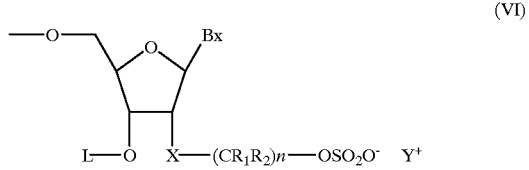

(VI)

wherein:

Bx is a heterocyclic base moiety;

Q is H or a hydroxyl protecting group;

L is H or a hydroxyl protecting group;

X is O, N or S;

$R_1$ and $R_2$ are independently H, alkyl, aryl, O-alkyl, O-aryl, carboxylic acid, amide, ester, halogen, trifluoromethyl, or amine;

n is 2–10; and,

Y is H,Li,Na,K,Cs or an amine.

These methods comprise:

selecting or providing a compound of formula V:

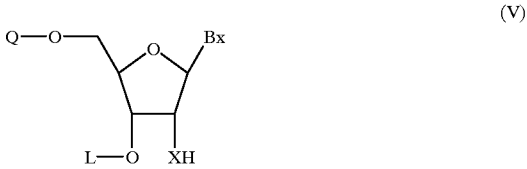

(V)

wherein:

Bx is a heterocyclic base moiety;

Q is H or a protecting group;

L is H or a protecting group; and

X is O, S or N; and, treating that compound with a compound of formula III, supra to give the desired compound of the formula VI. In conjunction with this embodiment, Bx is preferrably a purine or a pyrimidine base, optionally substituted with one or more protecting groups. In another preferred embodiment of the invention, the treating step includes reacting the compound of formula V in solution such as an aprotic solvent, for exmple, the preferred acetonitrile, dimethylacetamide, dimethylformamide, dimethylsulfoxide or tetrahydrofuran.

The solution is conveniently cooled from about 0° C. to about –78° C. and is then reacted with a base, especially the preferred metal hydride, metal hydroxide or metal carbonate. In a further preferred embodiment, the base is sodium hydride, potassium hydride, lithium hydride, sodium hydroxide, potassium hydroxide, lithium hydroxide, sodium carbonate, potassium carbonate or cesium carbonate. An especially preferred embodiment is the use of sodium hydride as the base. The solution is preferably warmed after addition of the base from about –78° C. to about 0° C. over about 5 minutes to about 60 minutes and then cooled from about 0° C. to about –78° C.

The solution is then treated with a cyclic sulfate, especially one which is substituted with one or more alkyl, aryl, O-alkyl, O-aryl, carboxylic acid, amide, ester, halogen, trifluoromethyl or amine functionalities. In another preferred embodiment, the solution is treated with an optionally substituted 5- or 6-membered ring cyclic sulfate. The solution is typically warmed from about 0° C. to about 20° C. over a period of from about 1 hour to about 24 hours to improve completeness of reaction.

The invention also provides methods for preparing compounds of formula VII:

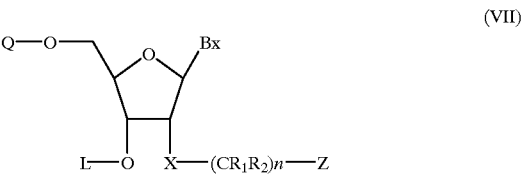

(VII)

wherein:

Bx is a heterocyclic base moiety;

Q is H or a protecting group;

L is H or a protecting group;

X is O, S or N;

$R_1$ and $R_2$ are independently H, alkyl, aryl, O-alkyl, O-aryl, carboxylic acid, amide, ester, halogen, trifluoro-methyl, or amine;

n is 2–10; and,

Z is H, amine, azide, halogen, thiol, O-alkyl, O-aryl, alkyl, aryl;

comprising the steps of:

providing a compound of the formula V;

(V)

wherein:

Bx is a heterocyclic base moiety;

Q is H or a protecting group;

L is H or a protecting group;

X is O, S or N; and, treating said compound of the formula V with a compound of the formula III,

wherein:

$R_1$ and $R_2$ are independently H, alkyl, aryl, O-alkyl, O-aryl, carboxylic acid, amide, ester, halogen, trifluoro-methyl, or amine; and, n is 2–10, to give an intermediate compound of the formula VI;

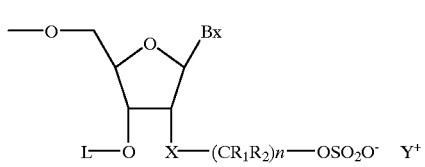

(VI)

wherein:
Bx is a heterocyclic base moiety;
Q is H or a hydroxyl protecting group;
L is H or a hydroxyl protecting group;
X is O, N or S;
$R_1$ and $R_2$ are independently H, alkyl, aryl, O-alkyl, O-aryl, carboxylic acid, amide, ester, halogen, trifluoromethyl, or amine;
n is 2–10;
Y is H,Li,Na,K,Cs or an amine; and,
reacting the resulting compound having formula VI with a nucleophile to yield the desired compound having formula VII.

The intermediate compound of formula VI is conveniently reacted with nucleophile at a temperature of from about 0° C. to about 200° C. for from about 1 hour to about 24 hours. The nucleophile is preferably an amine, such as the exemplary dimethylamine or similar materials. In another embodiment, the nucleophile is an alkoxide such as sodium methoxide or a thiol such as the preferred sodium thiomethoxide. The nucleophile may also be a diester of a malonic acid or similar species.

The invention also provides compounds of formula VI;

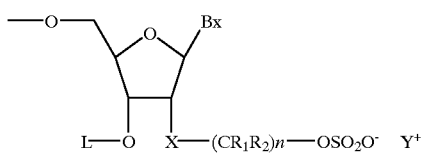

(VI)

wherein:
Bx is a heterocyclic base moiety;
Q is H or a hydroxyl protecting group;
L is H or a hydroxyl protecting group;
X is O, N or S;
$R_1$ and $R_2$ are independently H, alkyl, aryl, O-alkyl, O-aryl, carboxylic acid, amide, ester, halogen, trifluoromethyl, or amine;
n is 2–10;
Y is H,Li,Na,K,Cs or an amine.

Bx is a preferably a purine or a pyrimidine base optionally substituted with a protecting group such as thymine, N-3-protected-thymine, uracil, N-3-protected uracil, cytosine, adenine, 2,6-diaminopurine or guanine. In an especially preferred embodiment the N-3 protecting group is benzyloxymethyl.

The present invention is also directed to processes for modulating mRNA comprising the steps of incorporating into an oligomer a compound of the formula VII,

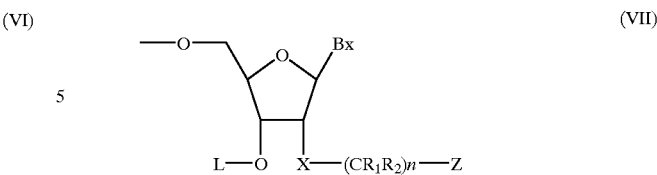

(VII)

wherein:
Bx is a heterocyclic base moiety;
Q is H or a protecting group;
L is H or a protecting group;
X is O, S or N;
$R_1$ and $R_2$ are independently H, alkyl, aryl, O-alkyl, O-aryl, carboxylic acid, amide, ester, halogen, trifluoro-methyl, or amine;
n is 2–10; and,
Z is H, amine, azide, halogen, thiol, O-alkyl, O-aryl, alkyl, aryl.

In a preferred embodiment of the invention, the heterocyclic base moiety is a purine or pyrimidine base optionally substituted with a protecting group.

The present invention provides methods of alkylation of carbohydrates, oligonucleotides, nucleotides and nucleosides that use a cyclic sulfate as an alkylating agent.

In the process of synthesizing a compound of the formula I,

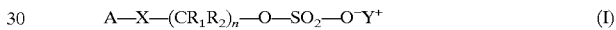

$$A-X-(CR_1R_2)_n-O-SO_2-O^-Y^+ \quad (I)$$

A can be a carbohydrate, an oligonucleotide, a nucleotide or a nucleoside. In particular, A can be a purine or a pyrimidine β-D-ribofiranosyl nucleoside or a purine or a pyrimidine β-D-2'-deoxyribofuranosyl nucleoside. The process of treating a compound of the formula II,

$$A-X-H \quad (II)$$

is conveniently done in a solution phase by the use of an aprotic solvent, including but not limited to acetonitrile, dimethylacetamide, dimethylformamide, dimethylsulfoxide or tetrahydrofuran. The solution is cooled from 0° C. to −78° C. to prevent excessive heat build up upon addition of the base. The base utilized can be a metal hydride, metal hydroxide or a metal carbonate. These bases include but are not limited to sodium hydride, potassium hydride, lithium hydride, sodium hydroxide, potassium hydroxide, lithium hydroxide, sodium carbonate, potassium carbonate or cesium carbonate. Most preferred is the use of sodium hydride as the base.

After addition of the base, the solution is conveniently allowed to warm to 0° C. to allow for complete anion formation. After between 5 and 60 minutes the base treated solution can be cooled from about 0° C. to about −78° C. Addition of a cyclic sulfate to the cooled base treated solution followed by warming to 0° C. to room temperature allows for the alkylation reaction to proceed. Typically, these reactions are allowed to go from one hour to 24 hours.

The product sulfate may be purified by evaporation of the solvent followed by column chromatography on silica gel using ethyl acetate or a gradient of 1% to 20% methanol in dichloromethane as the eluent to give the sulfonic acid. Further, the sulfonic acid may be treated with a base, including but not limited to triethylamine, to give the salt. Elution with 1 to 5% of an amine including but not limited to triethylamine, in the chromatography solvents gives the corresponding amine salt upon evaporation of the desired fractions.

The use of cyclic sulfates have not been found in the main stream of organic chemistry. Recently, however, they have begun to play a role in organic synthesis The parent five membered cyclic sulfite (ethylene sulfite) is most conveniently prepared from ethylene glycol and thionyl chloride (Breslow, D. S.; Skolnik, H., In Heterocyclic Compounds Interscience:

1966, p1 and references cited therein). Dichloromethane has been used to improve the yield (Garner, H. K.; Lucas, H. J.,*J. Am. Chem. Soc.*, 1950, 72, 5497). Several cyclic sulfites have been prepared by this method using thionyl chloride (Reibere, F.; Kagan, H. B., *Tetrahedron Lett.*, 1989, 30, 3659). Lohray has reported the synthesis of several substituted optically active cyclic sulfites by the reaction of homochiral diols with thionyl chloride (Lohray, B. B.; Ahuja, J. R., *J. Chem. Soc., Chem. Commun.*, 1991, 95).

The parent compound 1,3,2-dioxathiolane 2,2-dioxide (ethylene cyclic sulfate) was prepared by Baker and Field from 1,2-dibromoethane and silver sulfate in 23% yield whereas the reaction failed with 1,2-dibromopropane (Baker, W., Field, F. B., *J. Chem. Soc.*, 1932, 86). Alternatively, ethylene sulfate is obtained by the treatment of glycol diacetate with dimethyl sulfate (Breslow, D. S., Skolnik, H., In *Heterocyclic Compounds* Interscience: 1966, p1 and references cited therein). Unlike the synthesis of ethylene sulfite from ethylene glycol and thionyl chloride or ethylene oxide and sulfur dioxide (vide supra), the corresponding reaction with sulfuryl chloride or sulfur trioxide gave only low yields of ethylene sulfate. Thus, the treatment of ethylene glycol with sulfuryl chloride gave only 4% yield of ethylene sulfate (Pritchard, J. G.; Lauterbur, P. C., *J. Am. Chem. Soc.*, 1961, 83, 2105). Several cyclic sulfates of sugars and other polyhydroxylated compounds have been prepared with sulfuryl chloride and pyridine (Bragg, P. D.; Jones, J. K. N.; Turner, J. C., *Can. J. Chem.*, 1959, 37, 1412, and Jones, J. K. N.; Perry, M. B.; Turner, J. C., *Can. J. Chem.*, 1960, 38, 1122), however, the reaction has never been clean and several side products were isolated. For example, D-mannitol and dulcitol yielded tetrachloro-substituted cyclic sulfates (Robertson, F. M.; Neish, A. C., *Can. J Res.* 1947, 25B, 491). This is apparently due to the chlorinating nature of sulfuryl chloride (Tewson, T. J., *J. Org. Chem.*, 1983, 48, 3507, Tabushi, I.; Kitaguchi, H., In *Synthetic Reagents*, Pizey, J. S., Ed.; Ellis Horwood: Chichester, 1981, 4, 336). Similarly, the reaction of liquid sulfur trioxide with pinacolone gave only 36% yield of 4,4,5,5-tetramethyl-1,3,2-dioxathiolane 2,2-dioxide (Sheehan, J. C.; Zoller, U., *J. Org. Chem.*, 1974, 39, 3415). Garner and Lucas prepared trans-4,5-dimethyl-1,3,2-dioxathiolane 2,2-dioxide by oxidizing the corresponding cyclic sulfite prepared from (R,R)-(-)-2,3-butanediol with calcium permanganate (Garner, H. K.; Lucas, H. J., *J. Am. Chem. Soc.*, 1950, 72, 5497). The cis isomer was prepared using meso-2,3-butanediol (Robertson, F. M.; Neish, A. C., *Can. J. Res.*, 1947, 25B,491, Lichtenberger, J.; Hinckey, J., *Bull. Soc. Chim. Fr.*, 1961, 1495). Similarly, tetramethylene sulfate (Baker, W.; Burrow, B. F., *J. Chem. Soc.*, 1961, 2257) and cyclohexane 1,2-cyclic sulfate (Brimacombe, J. S.; Foster, A. B.; Hanwek, E. B.; Overend, W. G.; Staceus, M., *J. Chem. Soc.*, 1960, 201) were prepared by oxidizing the corresponding cyclic sulfites in moderate yield.

A good yield (74%) of cyclic sulfate has been reported by transesterification reaction of ethylene sulfite with sulfuric acid ($H_2SO_4$) to give 2-hydroxyethyl sulfuric acid followed by treatment with thionyl chloride (Tillett, J. G., *Phosphorous Sulfur*, 1976, 1341). Ethylene cyclic sulfate and the 4-butyl derivative have been prepared by the reaction of the corresponding olefin with phenyl iodosulfate ($PhIOSO_2O$) in 70–85% yield.

Highly substituted epoxides have been converted into cyclic sulfates in quantitative yield by the reaction with $H_2SO_4$ (Nishinaga, A.; Wakabayashi, S., *Chem Lett.*, 1978, 913). For example, 2,4,6-tri-tert-butyl-4,5-epoxy-6-5-diepoxy-6-hydroxy-2-cyclohexenone, when treated with equimolar amount of $H_2SO_4$ in acetic anhydride at ca. 0° C., the reaction was complete within 10 minutes to give 2,4,6-tri-tert-butyl-6-hydroxy-4,5-sulfonyldioxy-2-cyclohexenone. Similarly, the reaction of various epoxides with fluorosulfuric acid leads to the formation of fluorosulfates which readily cyclize in base to give the corresponding cyclic sulfates (Poorker, C. S.; Kagan, J., *Tetrahedron Lett.*, 1985, 26, 6405).

The reaction of dianions of diols with N,N-sulfuryl-diimidazole gives a better yield of cyclic sulfates (Tewson, T. J.; Soderlind, M. J., *Carbohydr. Chem.*, 1985, 4, 529), however, use of strong base such as sodium hydride is necessary to carry out this reaction. Lowe has reported the use of ruthenium tetraoxide, generated in situ from sodium periodate and rutheniom dioxide for the oxidation of the 1,2- and 1,3-cyclic sulfites to the corresponding cyclic sulfates under very mild conditions (Lowe, G.; Salamone, S. J., *J. Chem. Soc., Chem.* Commun., 1983, 1392, Lowe, G.; Salamone, S. J.; Jones, R. H., *J. Chem. Soc., Chem.* Commun., 1983, 266, Lowe, G.; Salamone, S. J., *J. Chem. Soc., Chem.* Commun., 1984, 466, Lowe, G.; Reed, M. A., *Tetrahedron Asymmetry*, 1990, 1, 885). This method has been used for the synthesis of several 1,2- and 1,3-cyclic sulfites to the corresponding cyclic sulfates under very mild conditions. This method had been used for the synthesis of several 1,2- and 1,3-cyclic sulfates in good yield (72–90%). Denmark has prepared 1,3-cyclic sulfate of a bicyclic system containing a 1,3-diol moiety via the stoichiometric ruthenium tetraoxide oxidation of the corresponding 1,3-cyclic sulfite in 72% yield (Denmark, S. E., *J. Org. Chem.*, 1981, 46, 3144). However, the use of a stoichiometric amount of ruthenium tetraoxide, which is expensive, for the oxidation of the cyclic sulfite, renders this method synthetically unattractive. Cyclic sulfites could also be oxidized by a catalytic amount of ruthenium tetroxide using sodium hypochlorite as the secondary oxygen transferring agent (LeRoy, P.; Mandard-Cazin, B., *Eur. Patent* EP 322521, 1988, *Chem. Abstr.*, 1990, 112, 77201, Takano, S.; Yanase, M., Ogasawara, K., *Chem. Lett.*, 1989, 1689). Cyclic sulfite has also been oxidized to sulfate in moderate yield (35–61%) in a biphasic miture of dichloromethane and aqueous acidic ($H_2SO_4$) potassium permanganate (Berridge, M. S.; Franceschini, M. P.; Rosenfeld, E.; Tewson, T. J., *J. Org. Chem.*, 1990, 55, 1211).

The difficulties in the preparation of cyclic sulfates account for their absence from the repertoire of main line synthetic organic chemistry, until recently, when a catalytic method for the oxidation of cyclic sulfites using ruthenium trichloride with sodium periodate was reported by Sharpless (Gao, Y.; Sharpless, K. B., *J. Am. Chem. Soc.*, 1988, 110, 7538). This is the most general method for the synthesis of cyclic sulfates in excellent yield (72–100%).

Recently, using this method, various substituted cyclic sulfates have been reported. For example, Van Boom et al reported the synthesis of 1,4-cyclic sulfates of sugar derivatives from the corresponding cyclic sulfites in 85% yield (Van der Klein, P. A. M.; Boons, G. J. P. H.; Veeneman, G. H.; Van der Marel, G. A.; Van Boom, J. H., *Tetrahedron Lett.*, 1989, 30, 5477, Van der Klein, P. A. M.; Boons, G. J. P. H.; Veeneman, G. H.; Van der Marel, G. A.; Van Boom, J. H., Synlett, 1990, 311). Similarly, Kibayashi and Machinaga have reported the synthesis of 6-butyl-3-pentyl substituted 1,4-cyclic sulfates from the corresponding diols by the reported one-pot procedure of conversion of diols to cyclic sulfates in 77% overall yield (Machinga, N.; Kibayashi, C., *Tetrahedron Lett.*, 1990, 31, 3637). Vandewalle has prepared cyclic sulfates from 1,2-diols derived from carbohydrates in 91% overall yield (Vannessche, K.; Van der Kycken, E.; Vandewalle, M.; Roper, H., *Tetrahedron Lett.*, 1990, 31, 2337).

The oxidation reaction can be carried out in the presence of acid or base labile functional groups, such as acetals or ketals, however, the reaction fails in the presence of functional groups which can bind with ruthenium tetraoxide and therefore, stop the catalytic turnover (Kim, B. M.; Sharpless, K. B., *Tetrahedron Lett.*, 1989, 30, 655, Goren, M. B.; Kochansky, M. E., *J. Org. Chem.*, 1973, 38, 3510, Kim, B. M.; Sharpless, K. B., *Tetrahedron Lett.*, 1990, 31, 4317). For example, oxidation of certain cyclic sulfates containing an amide functionality could not be carried out under the conditions reported by Gao and Sharpless (Gao, Y.; Sharpless, K. B., *J. Am. Chem. Soc.*, 1988, 110, 7538). Recently, some of the cyclic sulfamidates have been prepared from amino alcohols via the oxidation of the corresponding sulfimidites, which in turn can be easily prepared by the reaction of thionyl chloride with amino alcohols (Cyclic sulphamidates: Noda, Y., *Bull. Chem. Soc. Jpn.*, 1967, 40, 1554).

Some of the cyclic sulfates known in the literature are listed in Lohray, B. B., *Synthesis*, 1992, 1035.

Cyclic sulfates are convenient, versatile, readily available and reactive alkylating agents. Simple 5 and 6 membered ring cyclic sulfates are commercially available for example, 1,3,2-dioxathiolane 2,2-dioxide and 1,3,2-dioxathiane 2,2-dioxide (Aldrich). There are many examples of alcohols that can be converted into cyclic sulfates by methods known in the art (Lohray, B. B., *Synthesis*, 1992, 1035). Cyclic sulfates may be optionally substituted with including but not limited to various alkyl, aryl, O-alkyl, O-aryl, carboxylic acid, amide, ester, halogen, trifluoromethyl or amine functionalities. Further, the size of the ring and the substituents attached to the cyclic sulfate determines the chain length and nature of the alkylated products.

Cyclic sulfates can be considered to be epoxide like synthons in some respects. Cyclic sulfates and epoxides are both highly reactive in that both undergo ring opening in the presence of a nucleophile. A nucleophile can attack the α-carbon atom of a cyclic sulfate or an epoxide in an $S_N2$ fashion to give an alkylated product with inversion of configuration. Both cyclic sulfates and epoxides are usually superior to their acyclic counter parts because of their cyclic nature which renders the competing elimination process stereoelectron-ically unfavorable. Cyclic sulfates may act as an alkylating agent to afford after acid hydrolysis of the sulfate, a product alcohol with a variety of chain lengths including but not limited to a 2, 3 or 4 carbon atom homologation. By their nature, however, epoxides are limited to give a β-substituted alcohol(Lohray, B., *Synthesis*, 1992, 11, 1035).

The reactivity of cyclic sulfates and epoxides towards nucleophiles are similar in nature due to their similar properties. The high reactivity of cyclic sulfates has been contributed to ring strain, even though the origin of the ring strain is not clear. It has been speculated that the possible cause of ring strain might be due to (a) angle strain (b) partial double bond character between ring oxygen and sulfur due to the 2p(O)-3d(S) orbital interaction (c) 1,3-nonbonding interactions between the ring oxygen and the exocyclic oxygen (Tillet, J. G., *Phosphorous Sulfur*, 1976, 1341). In addition to ring strain the good leaving ability of the $ROSO_3^-$ moiety makes the cyclic sulfate very reactive towards various reagents.

Cyclic sulfates, however, are more reactive than epoxides and undergo $S_N2$ type reactions with nucleophiles with inversion of configuration. Although the ring strain is greater for an epoxide (ca. 27–28 Kcal/mol)than it is for a 5-membered cyclic sulfate (ca. 5–6 Kcal/mol), the cyclic sulfate is much more reactive and undergoes nucleophilic attack under acidic, basic and neutral conditions without the help of any catalysts. Epoxides are usually much less reactive than the cyclic sulfate and may require Lewis acids to catalyze the ring opening reaction. The difference in reactivity may be a reflection of the leaving group ability of an $ROSO_3^-$ group in a cyclic sulfate being much greater than it is for an $RO^-$ in an epoxide. Generally, the nucleophile usually attacks the less hindered C—O bond for both cyclic sulfates and epoxides. The difference in regioselectivity for nucleophilic attack of ethylene cyclic sulfate and ethylene oxide in some cases are complimentary to each other. For α,β substituted esters, the nucleophile attacks the α carbon for cyclic sulfates and the β carbon for epoxides.

Cyclic sulfates undergo nucleophilic ring opening in the presence of oxygen, sulfur, halogen, nitrogen, hydride and C nucleophiles. These nucleophiles include but are not limited to alcohols, alkoxides, amines, azides, benzoates, halogens, hydrides, isothiocyanates, nitro, malonate esters and organometallic reagents including Grignard reagents such as benzyl magnesium chloride. Cyclic sulfates of aliphatic 1,2-diols are powerful alkylating agents towards a series of O-nucleophiles. Cyclic sulfates react readily with phenolates, amine oxides or carboxylates to furnish the corresponding alkylated products in high yields (Berridge, M. S.; Franceschini, M. P.; Rosenfeld, E.; Tewson, R. J., *J. Org. Chem.*, 1990, 55, 121 1, Gao, Y.; Sharpless, K. B., *J. Am. Chem. Soc.*, 1988, 110, 7538, Vanessche, K.; Van der Kycken, E.; Vandewalle, M.; Roper, H., *Tetrahedron Lett.*, 1990, 31, 2337, Tomalia, D. A.; Falk, J. C., *J. Heterocycl. Chem.*, 1972, 9, 891).

It should be noted that a double nucleophilic displacement is possible with a cyclic sulfate whereas only a single nucleophilic displacement is possible with an epoxide. In all cyclic sulfate openings the first formed product is a sulfate, which may be hydrolyzed to the hydroxy compound by treatment with a two phase mixture of ether and 20% sulfuric acid at 25° C. for 6–12 h with stirring. It is in this sense that cyclic sulfates are somewhat synthetically equivalent to epoxides. However, unlike the hydroxyl group generated in epoxide openings, the corresponding sulfate moiety is still a leaving group and can serve as such in certain situations. As such, cyclic sulfates may also undergo a double nucleophilic displacement reaction. Previously, these were limited to intramolecular double nucleophilic displacement reactions, for example, the formation of cyclopropanes from malonate anions and aziridines from primary amines (Gao, Y.; Sharpless, K. B. *J. Am. Chem. Soc.* 1989, 110, 7538).

An embodiment of the invention provides methods for preparing a compound of the formula I;

$$A-X-(CR_1R_2)_n-O-SO_2-O^-Y^+ \qquad (I)$$

wherein:

A is a carbohydrate, an oligonucleotide, a nucleotide, or a nucleoside;

X is a O, S, or N;

$R_1$ and $R_2$ are independently H, alkyl, aryl, O-alkyl, O-aryl, carboxylic acid, amide, ester, halogen, trifluoro-methyl, or amine;

n is 2–10; and,

Y is H,Li,Na,K,Cs or an amine.

The desired alkylation of the substrate carbohydrate, oligonucleotide, nucleotide or nucleoside is accomplished by first selecting a compound of the formula II,

   (II)

wherein:

A is a carbohydrate, an oligonuclcotide, a nucleotide, or a nucleoside;

X is a O, S, or N.

Treatment of the compound of formula II with a cyclic sulfate of formula III;

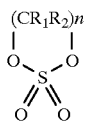

wherein:

$R_1$ and $R_2$ are independently H, alkyl, aryl, O-alkyl, O-aryl, carboxylic acid, amide, ester, halogen, trifluoromethyl, or amine; and, n is 2–10, gives the compound of formula I,

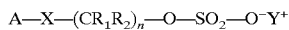   (I)

which is a versatile intermediate in the synthesis of modified sugars, having a utility which is apparent from the present specification.

Another embodiment of the invention provides methods for preparing a compound of formula IV;

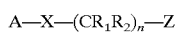   (IV)

wherein:

A is a carbohydrate, an oligonucleotide, a nucleotide, or a nucleoside;

X is a O, S, or N;

$R_1$ and $R_2$ are independently H, alkyl, aryl, O-alkyl, O-aryl, carboxylic acid, amide, ester, halogen, trifluoromethyl, or amine;

n is 2–10; and,

Z is H, amine, azide, halogen, thiol, O-alkyl, O-aryl, alkyl, aryl;

comprising the steps of:

selecting a compound of formula II; and,

   (II)

wherein:

A is a carbohydrate, an oligonucleotide, a nucleotide, or a nucleoside;

X is a O, S, or N; and, treating that compound with a compound of formula III,

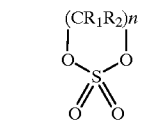   (III)

wherein:

$R_1$ and $R_2$ are independently H, alkyl, aryl, O-alkyl, O-aryl, carboxylic acid, amide, ester, halogen, trifluoromethyl, or amine; and, n is 2–10.

Reaction of the intermediate of formula I;

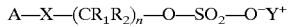   (I)

with an appropriate nucleophile gives the alkylated product IV.

   (IV)

The nucleophiles that may be utilized to displace the sulfate includes but is not limited to alkoxides, amines and thiols. Other nucleophiles include suitable for displacing a sulfate include but are not limited to alcohols, azides, benzoates, halogens, hydrides, isothiocyanates, nitro, malonate esters and organometallic reagents including Grignard reagents such as benzyl magnesium chloride.

Intermolecular nucleophilic displacement of the intermediate sulfate may be accomplished in a one pot reaction by addition of a nucleophile and heating from about 30° C. to about 200° C. Alternatively, the intermediate sulfate may be isolated by silica gel column chromatography by elution with ethyl acetates or a gradient of 1% to 20% methanol in dichloromethane to give the corresponding sulfonic acid. The sulfonic acid may be treated with a base including but not limited to triethylamine to afford the corresponding salt. Elution with about 1–5% triethylamine present in the solvents in the chromatography and subsequent evaporation gives the product sulfate as the triethylamine salt. Nucleophilic displacement of the sulfate acid or salt may be accomplished by heating the sulfate moiety in the presence of a nucleophile from about 30° C. to about 200° C.

An embodiment of the invention also provides methods of alkylation of nucleotides and nucleosides by the use of a cyclic sulfate as an alkylating agent. A process is described for preparing a compound of the formula VI;

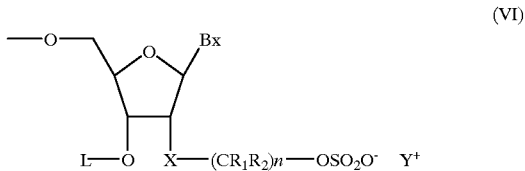   (VI)

wherein:

Bx is a heterocyclic base moiety;

Q is H or a hydroxyl protecting group;

L is H or a hydroxyl protecting group;

X is O, N or S;

$R_1$ and $R_2$ are independently H, alkyl, aryl, O-alkyl, O-aryl, carboxylic acid, amide, ester, halogen, trifluoro-methyl, or amine;

n is 2–10; and,

Y is H,Li,Na,K,Cs or an amine;

comprising the steps of:

selecting a compound of the formula V;

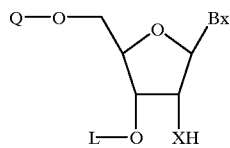

(V)

wherein:

Bx is a heterocyclic base moiety;

Q is H or a protecting group;

L is H or a protecting group;

X is O, S or N; and, treating said compound of the formula V with a compound of the formula III;

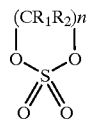

wherein:

$R_1$ and $R_2$ are independently H, alkyl, aryl, O-alkyl, O-aryl, carboxylic acid, amide, ester, halogen, trifluoro-methyl, or amine; and, n is 2–10, to give a compound of the formula VII.

Another embodiment of the invention provides methods for displacing the intermediate sulfate of the formula VI,

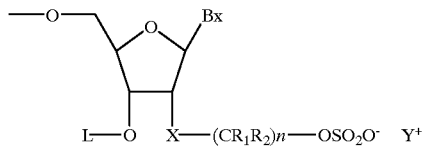

(VI)

wherein:

Bx is a heterocyclic base moiety;

Q is H or a hydroxyl protecting group;

L is H or a hydroxyl protecting group;

X is O, N or S;

$R_1$ and $R_2$ are independently H, alkyl, aryl, O-alkyl, O-aryl, carboxylic acid, amide, ester, halogen, trifluoro-methyl, or amine;

n is 2–10; and,

Y is H,Li,Na,K,Cs or an amine; formed upon reaction of a nucleotide or nucleoside with a cyclic sulfate.

Displacement of the intermediate sulfate of the formula VII with a nucleophile gives a modified nucleotide or nucleoside of the formula VII.

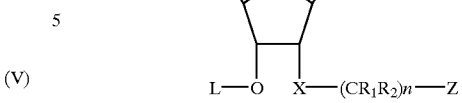

(VII)

Another embodiment of the invention is directed to methods for preparing compounds of the formula VII;

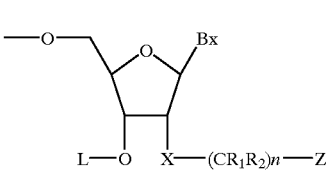

(VII)

wherein:

Bx is a heterocyclic base moiety;

Q is H or a protecting group;

L is H or a protecting group;

X is O, S or N;

$R_1$ and $R_2$ are independently H, alkyl, aryl, O-alkyl, O-aryl, carboxylic acid, amide, ester, halogen, trifluoromethyl, or amine;

n is 2–10; and,

Z is H, amine, azide, halogen, thiol, O-alkyl, O-aryl, alkyl, aryl;

comprising the steps of:

selecting a compound of the formula V;

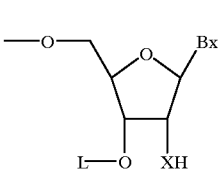

(V)

wherein:

Bx is a heterocyclic base moiety;

Q is H or a protecting group;

L is H or a protecting group;

X is O, S or N; and, treating said compound of the formula V with a compound of the formula III;

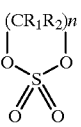

wherein:

$R_1$ and $R_2$ are independently H, alkyl, aryl, O-alkyl, O-aryl, carboxylic acid, amide, ester, halogen, trifluoro-methyl, or amine; and, n is 2–10, to give an intermediate of the formula VI,

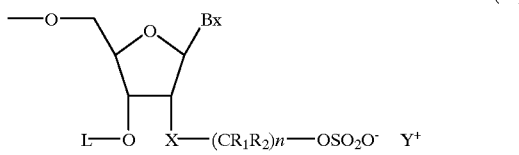

wherein:
Bx is a heterocyclic base moiety;
Q is H or a hydroxyl protecting group;
L is H or a hydroxyl protecting group;
X is O, N or S;
R$_1$ and R$_1$ are independently H, alkyl, aryl, O-alkyl, O-aryl, carboxylic acid, amide, ester, halogen, trifluoro-methyl, or amine;
n is 2–10;
Y is H,Li,Na,K,Cs or an amine; and,
reacting said intermediate of the formula VI with a nucleophile to give a compound of the formula VII.

The methods described allow for an alkylation at the 2', 3' or 5'-hydroxyl positions of the sugar moiety of a nucleoside with a cyclic sulfate. The present methods allow for a regioselective alkylation of the 2'-O position of the free 2'-, 3'- and 5'-hydroxyl nucleosides. In Example 1 (FIG. 1), the alkylation of N-3-(benzyloxy)methyl-5-methyluridine with the 5-membered cyclic sulfate, 1,3,2-dioxathiolane 2,2-dioxide, gives a 44% yield of a chromatographically separable 4 to 1 mixture of the 2'-O-ethylsulfonic acid sodium salt-N-3-(benzyloxy)methyl-5-methyluridine 1, and the 3'-O-ethylsulfonic acid sodium salt-N-3-(benzyloxy)methyl-5-methyluridine 2, with none of the 5' O-alkylated product detected. Similarly, in Example 2 (FIG. 2), the 6-membered ring cyclic sulfate, 1,3,2-dioxathiane 2,2-dioxide, gives a 42% yield of a chromatographically separable 4 to 1 mixture of the 2'- to 3'-O-alkylated products 3 and 4, exclusively. The 2'-O-alkylated regioselectivity was determined by a 2D $^1$H NMR TOCSY experiment.

This selective alkylation allows for the elimination of the protection and subsequent deprotection steps when alkylating the 2'-O-position of nucleosides. Alkylation of the pyrimidine or the purine ring was not observed in any of these syntheses. The regioselective alkylation reactions were reproduced on multigram scales (25 g), and the small amounts of 3'-O-isomer were readily separated by silica gel column chromatography as described in the experimental section. The product sulfates can either be isolated as their corresponding salts including but not limited to sodium and triethylamine salts or their sulfonic acids. Further, nucleophilic displacement of the sulfate can be done with either the corresponding salts including but not limited to sodium and triethylamine salts or the sulfonic acids.

Unprotected nucleosides are regioselectively alkylated using methods of the present invention. Direct alkylation is faster and less expensive eliminating protection and deprotection. There has been ample work published on this subject involving activated (Takaku et al., Chem. Lett., 1982, 189) and unactivated electrophiles(Manoharan et al., Tetrahedron Lett., 1991, 32, 7171). The degree of selectivity encompasses a wide range and appears to depend on the substrate and/or the electrophile.

An embodiment of the invention uses various hydroxyl protecting groups known in the art, to afford selective alkylations. A convenient bifunctional silyl group known as the Markiewicz reagent is tetra(isopropyldisilozane)-1,3-diyl (TIPDSi) which allows for a selective and simultaneous 3',5'-hydroxyl protection of nucleosides in high yields. Thus, 1,3-dichloro-1,1,3,3-tetra(isopropyldisiloxane)(TIPDSiCl$_2$), reacts with nucleosides initially at the 5'position and then cyclizes with the 3' position to yield the corresponding 3',5'-O-TIPDSi-disilyl nucleoside derivative. The TIPDSi group has been used for 3',5'-protection of a variety of nucleosides and nucleotides (Markiewicz, W. T.; Wiewiorowski, M., Nucleic Acids Res. Spec. Publ., 1978, S158, Robins, M. J.; Wilson, J. S.; Hansske, F., J. Am. Chem. Soc., 1983, 105, 4059, Giocli, C.; Kwiatkowski, M.; Oberg, B.; Chattopadhyaya, J. B., Tetrahedron Lett., 1981, 22, 1741, Pankiewicz, K. W.; Watanabe, K. A.; Takayanagi, H.; Itoh, T.; Ogura, H., J. Heterocycl. Chem., 1985, 22, 1703, Pankiewicz, K. W.; Watanabe, K. A., Nucleic Acids Res. Symp. Ser., 1982, 11, 9). Some bis-silyl protected nucleosides are commercially available (Aldrich), for example, 3',5'-O-(1,1,3,3-tetraisopropyl-1,3-disiloxanediyl)adenine or 3',5'-O-(1,1,3,3-tetraisopropyl-1,3-disiloxanediyl) cytidine. Thus, the free 2'-hydroxyl is available to react with a cyclic sulfate without competition from the 3' and 5'-hydroxyl groups.

It is also known in the art that the 2',3'-cis-hydroxyl positions of ribonucleosides are protected by forming the 2',3'-O-alkylidene (Hampton, A., J. Am. Chem. Soc., 1961, 83, 3640, Chladek, S.; Smrt, J., Coll. Czech. Chem., 1963, 28, 1301, Hampton, A.; Fratantoni, J. C.; Carroll, P. M.; Wong, S., J. Am. Chem. Soc., 1965, 87, 5481), arylidene (Chladek, S.; Smrt, J., Coll. Czech. Chem., 1963, 28, 1301, Hampton, A.; Fratantoni, J. C.; Carroll, P. M.; Wong, S., J. Am. Chem. Soc., 1965, 87, 5481, Smith, M.; Rammler, D. H.; Goldberg, P. M.; Khorana, H. G., J. Am. Chem. Soc., 1964, 84, 430, Cramer, F.; Saenger, W.; Scheit, K.; Tennigkeit, J., Ann. Der Chemie, 1964, 679, 156), or orthoester (Zemlicka, J., Chem. Ind. (London), 1964, 581, Jarman, M.; Reese, C. B., Chem. Ind. (London), 1964, 1493, Reese, C. B.; Sulston, J. E., Proc. Chem. Soc., 1964, 214) derivatives which are all acid labile and have found considerable use in nucleoside chemistry. Commercially available nucleosides include but are not limited to 2',3'-isopropylideneadenosine (Aldrich) which may also be utilized in the cyclic sulfate alkylation. This allows for a free 5'-hydroxyl nucleoside to react with a cyclic sulfate to give an alkylated nucleoside exclusively at the 5'-O position.

Selective protections of the 2'- and 5'-hydroxyl positions allow the 3'-hydroxyl position available to react with a cyclic sulfate. The 5'-hydroxyl may be preferentially protected as the acid labile triphenylmethyl (trityl) group or the tert-butyldimethylsilyl derivative and the 2'-hydroxyl as the tert-butyldimethylsilyl group (Ogilvie, K. K., in Nucleosides, Nucleotides and Their Biological Applications, Academic Press, New York, 1983, Jones, S. S.; Reese, C. B., J. Chem. Soc. Perkins Trans. 1, 1979, 2762). Thus, the free 3'-hydroxyl is available to react with a cyclic sulfate to give an alkylated nucleoside exclusively at the 3'-O position.

The resultant alkylated nucleoside sulfates may be isolated as the corresponding salt or acidified to give the sulfonic acid. The intermediate sulfate may be hydrolyzed to the hydroxy compound by treatment with a two phase mixture of ether and 20% sulfuric acid at 25° C. for 6–12 h with stirring as previously described. The corresponding alcohol may be further elaborated by methods known in the art. The resultant 2'-O-hydroxyethyl nucleosides can be further reacted with reagents to form derivative compounds such as 2'-O-methoxyethyl (2'-O-MOE) and 2'-O-dimethylaminoethyl (DMAOE) nucleosides. The preparation of derivative nucleosides from the 2'-O-hydroxyethyl nucleoside is disclosed in PCT application PCT/US 98/02405, entitled "Aminooxy-Modified Oligonucleotides," filed Feb. 13, 1998. For example, the 2'-O-hydroxyethyl compounds can be converted into their respective 2'-O-$CH_2CH_2$—O-tosylate derivatives by treatment with 1 equivalent of p-toluenesulfonyl chloridepyridine. The tosylate is subsequently treated with one of several amino-hydroxy compounds that are effective nucleophiles in displacing tosylate to yield a series of oxy-amino compounds. The reaction is facilitated by preforming the anion from the amino alcohol or hydroxylamine derivative by the use of sodium hydride under anhydrous conditions.

In another embodiment of the invention, an amine is used as the nucleophile to displace the intermediate sulfate. In Example 3a (FIG. 3), dimethylamine is used as the nucleophile to displace the sulfate moiety of 2'-O-propyl-sulfonic acid sodium salt-N-3-(benzyloxy)methyl-5-methyluridine 3. Heating of the intermediate sulfate 3 with 2.0 M dimethylamine in tetrahydrofuran at 140° C. for 20 hours in a steel bomb gives the 2'-O-(N,N-dimethylpropyl)-N-3-(benzyloxy)methyl-5-methyluridine 5 in 36% yield. The benzyloxymethyl group is removed by a palladium hydroxide on carbon reduction in the presence of hydrogen as described in Example 3b (FIG. 3) to give 2'-O-(N,N-dimethylpropyl)-5-methyluridine 6.

The 2'-O-[2-(N,N-dimethyl)aminopropyl]-5-methyluridine 6 is protected at the 5'-hydroxyl position with 4,4'-dimethoxytrityl chloride (DMTCl)to give 5'-O-DMT-2'-O-[2-(N,N-dimethyl)aminopropyl]-5-methyluridine 7 as described in Example 4a (FIG. 4). 7 is converted into 5'-O-DMT-2'-O-[2-(N,N-dimethyl)aminopropyl]-5-methyluridine-3'-O-[(2-cyanoethyl)N,N-diiopropyl] phosphoramidite 8 as described in Example 4b (FIG. 4) for use in oligonucleotide synthesis.

The development of phosphite triester (now often called phosphoramidite) chemistry by Caruthers and co-workers transformed oligonucleotide synthesis from a manual procedure carried out by a few specialists into a commercialized process performed using a machine (Caruthers, M. H., *Science*, 1985, 281). The crux of this chemistry is a highly efficient coupling reaction between a 5'-hydroxyl group of a support-bound deoxynucleoside and an alkyl 5'-DMTr-(N-2-cyanoethyl)-deoxy-nucleoside 3'-O-(N,N-diisopropylamino)phosphite. In early development of this chemistry, a chlorophosphite was used in place of the N,N-diidopropoylaminophosphite, but was found to be too unstable upon storage. By contrast, a phosphoramidite is considerably less reactive and requires protonation at nitrogen to make the phosphoramidite into a highly reactive phosphitylating agent. Tetrazole is just sufficiently acidic to do this without causing loss of the DMTr group. The product of coupling is a dinucleoside phosphite, which must be oxidized with iodine to the phosphotriester before proceeding with chain extension. The efficiency of coupling is reported to be extremely high (>98%).

Figure 5:
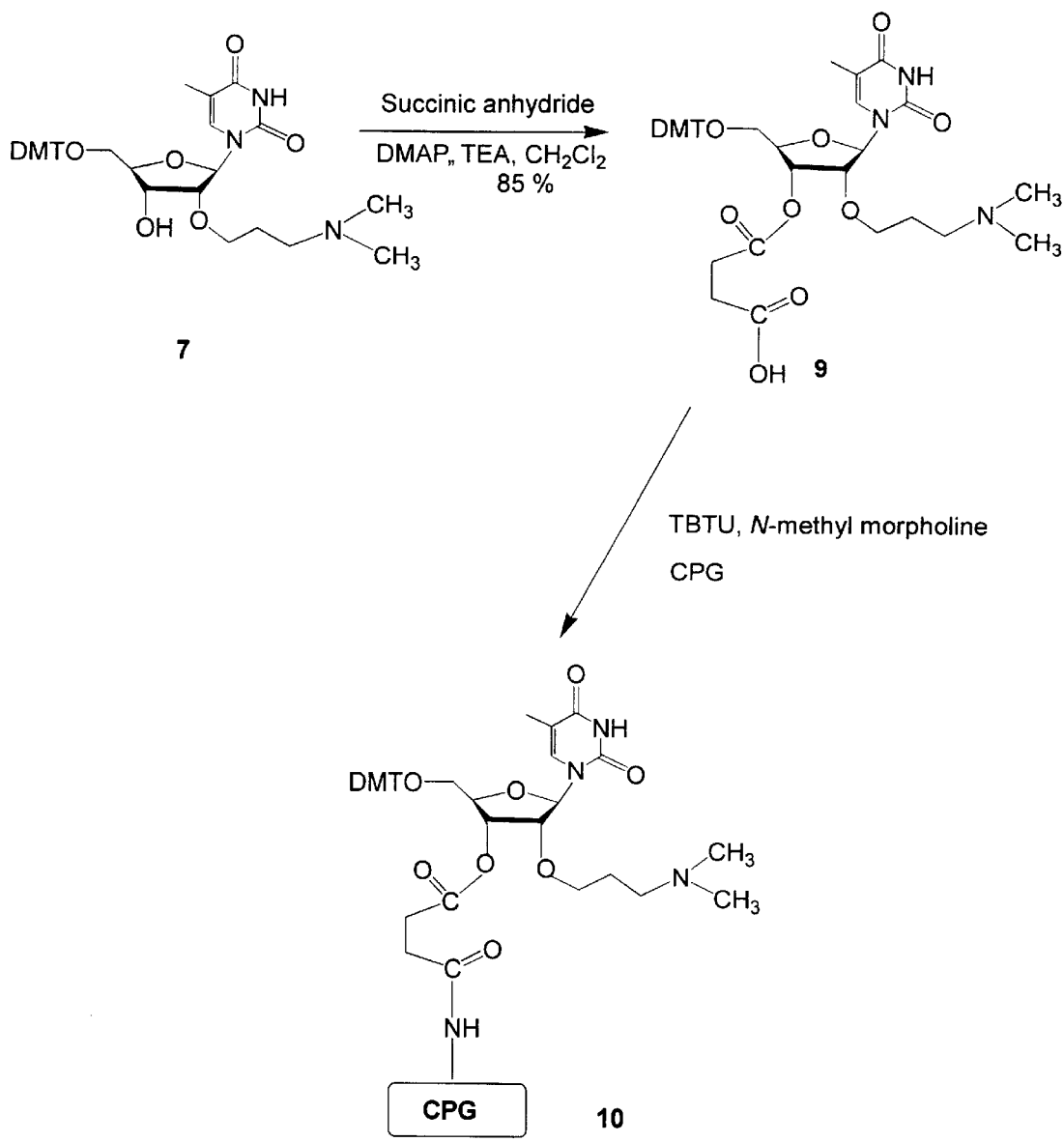

The 5'-O-DMT-2'-O-[2-(N,N-dimethyl)aminopropyl]-5-methyluridine 7, is reacted with succinic anhydride and the resulting acid 9 is attached to a solid phase support to give 10 as described in Examples 5a and 5b (FIG. 5).

Solid-phase synthesis uses a heterogeneous coupling reaction between a deoxynucleotide derivative in solution and another residue bound to an insoluable support. This has the advantage that a large excess of the soluble deoxynucleotide can be used to force the reaction to high yields. The support-bound product dinucleotide can be removed from the excess of reactant mononucleotide simply by filtration and washing. This process is far faster than a conventional separation technique in solution and easily lends itself to mechanization.

Controlled pore glass beads (CPG) as a support for solid phase oligonucleotide synthesis has proved to be useful under all conditions and with all chemistries. CPG beads are ideal in being rigid and non-swellable. They are manufactured with different particle sizes and porosities, and they are chemically inert to reactions involved in oligonucleotide synthesis. Currently, 500 and 1000 A porosities are favored. The CPG is functionalized with silyl groups attached to a long chain alkylamine. This spacer is used to extend the sites away from the surface and ensure accessibility to all reagents. The loading of amino groups on the glass is best kept with a narrow band of 10–50 umol g$^{-1}$, below which the reactions become unreproducible and above which they are subject to steric crowding between the chains. The 3'-terminal deoxynucleoside of the oligonucleotide to be synthesized is attached to the CPG support by conversion of its 5'-O-DMTr-(N-acylated)-derivative into the corresponding 3'-O-succinate, which is subsequently reacted with amino groups on the support (Gait, M. J., *Oligonucleotide synthesis: a practical approach.*, 1984, IRL Press, Oxford).

Other nucleophiles useful in the invention for displacing the sulfate moiety includes thiols. As shown in Examples 6a and 6b (FIG. 6), 2'-O-Ethyl-sulfonic acid sodium salt-N-3-(benzyloxy)methyl-5-methyluridine 1 is first deprotected using a catalytic amount of 10% palladium hydroxide on carbon in the presence of 55 psi of hydrogen. The 2'-O-ethyl-sulfonic acid sodium salt-5-methyluridine 11 is treated with an excess of sodium thiomethoxide in DMF at 80° C. for 24 hours to give the alkylated product 2'-O-[2-(thiomethyl)ethyl]-5-methyluridine 12 in 56% yield.

Figure 7:
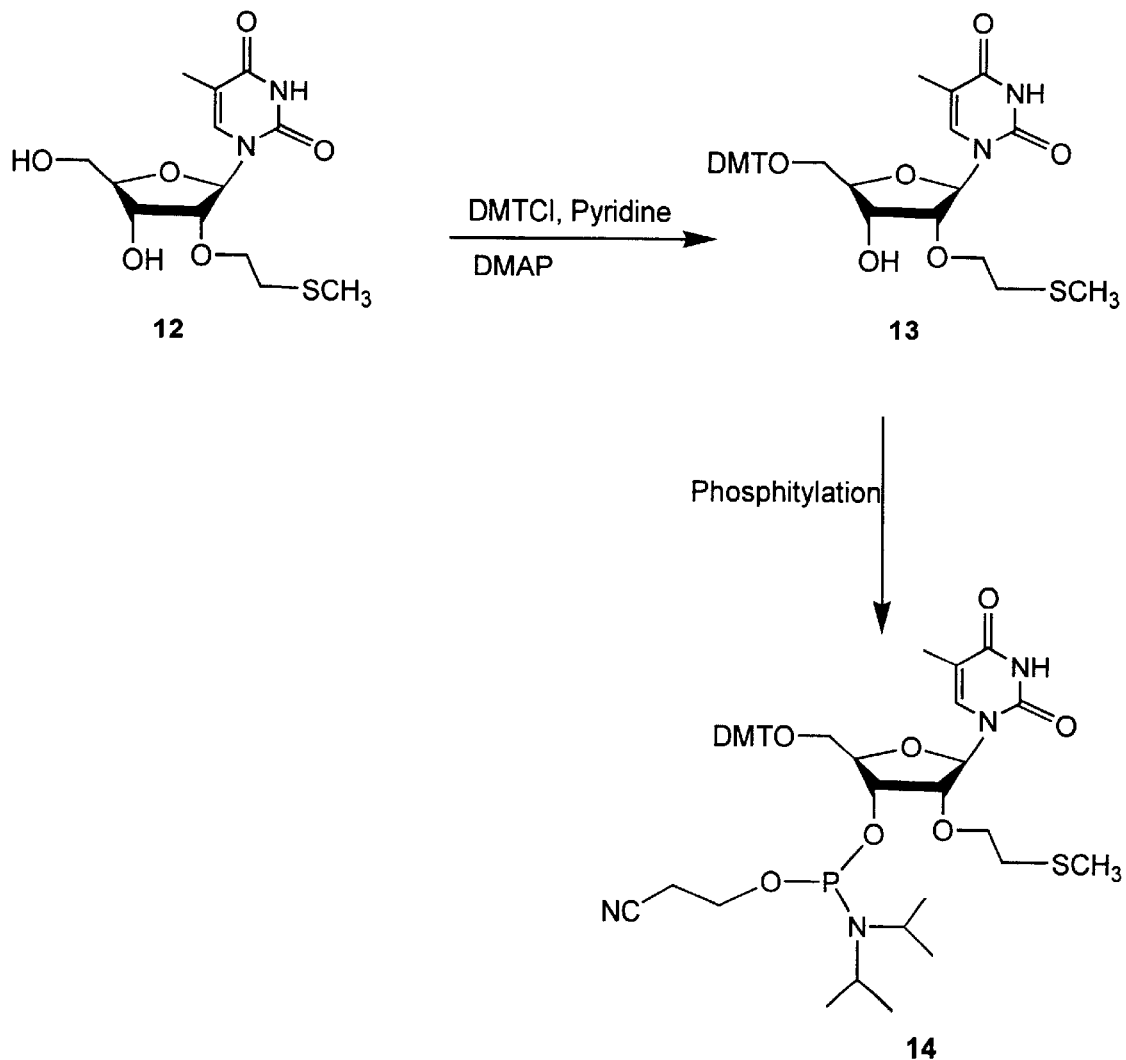
FIG. 7 Protection of the 5'-hydroxyl of 2'-O-[2-(thiomethyl)ethyl]-5-methyluridine 12 with 4,4'-dimethoxytrityl chloride (DMTCl) and phosphitylation of 5'-O-DMT-2'-O-[2-(thiomethyl)ethyl]-5-methyluridine 13.

2'-O-[2-(thiomethyl)ethyl]-5-methyluridine 12 is protected at the 5'-hydroxyl position with 4,4'-dimethoxytrityl chloride (DMTCl)to give 13 as described in Example 7a (FIG. 7). The 3'-hydroxyl group is then converted into the phosphoramidate, 5'-O-DMT-2'-O-[2-(thiomethyl)ethyl]-5-methyluridine-3'-O-[(2-cyanoethyl)N,N-diiopropyl] phosphoramidite 14, for use in oligonucleotide synthesis as described in Example 7b (FIG. 7).

Figure 8:
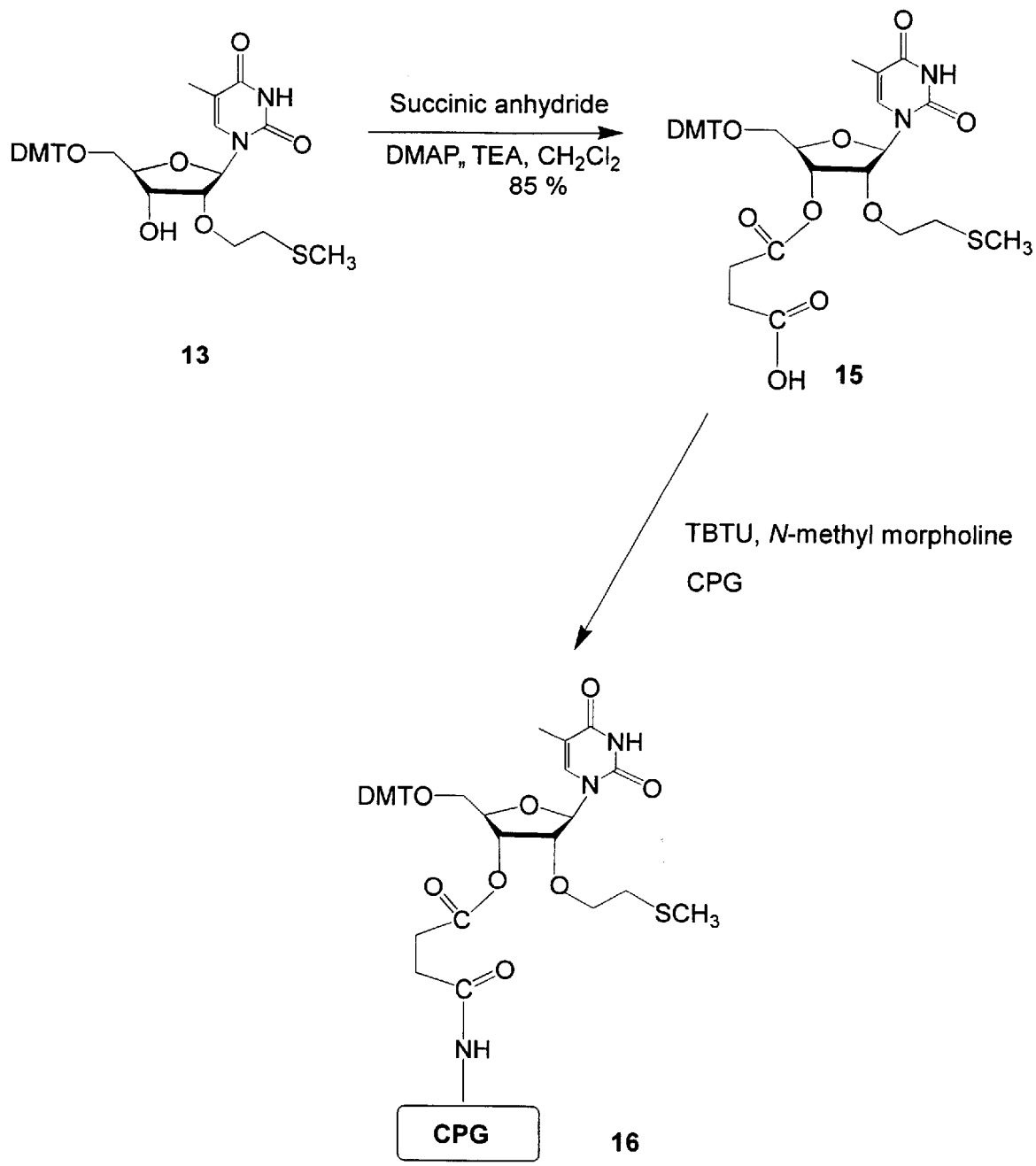

The 5'-O-DMT-2'-O-[2-(thiomethyl)ethyl]-5-methyluridine 13, is reacted with succinic anhydride and the resulting acid 15 is attached to CPG to give 16 as described in Examples 8a and 8b (FIG. 8).

Figure 9:
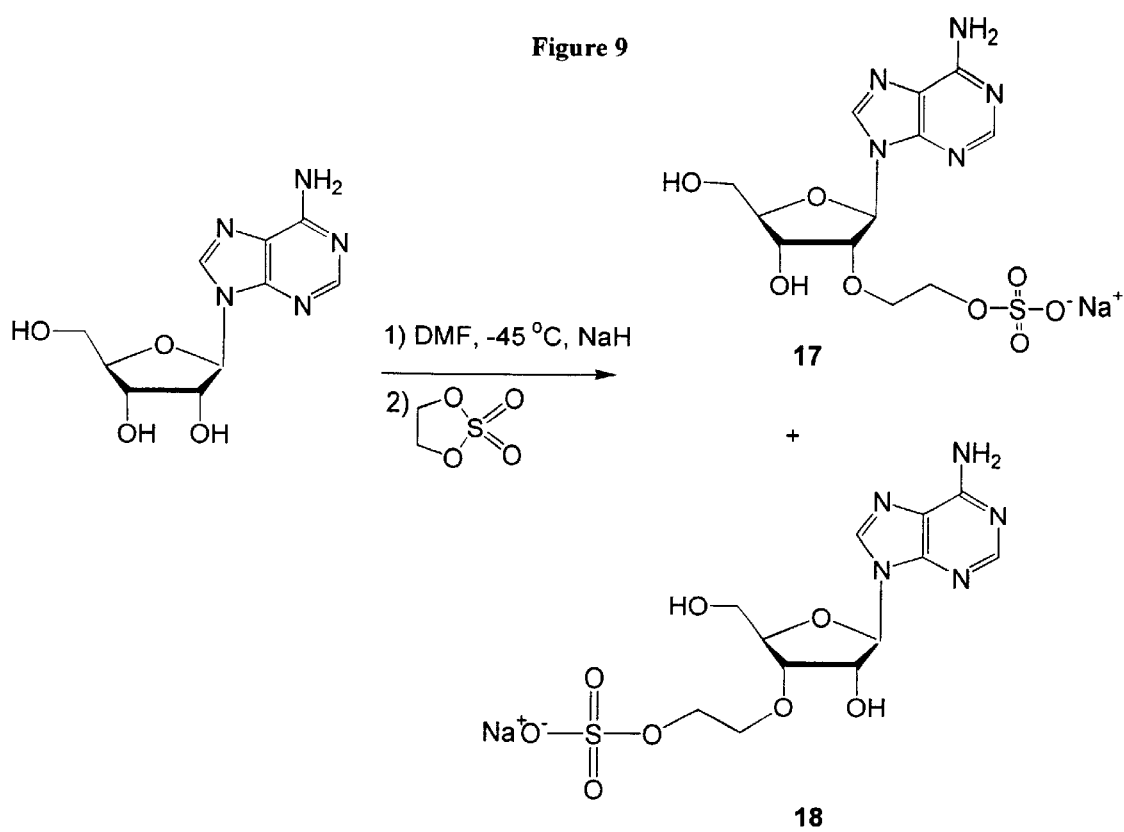
FIG. 9 Alkylation of adenosine with 1,3,2-dioxathiolane 2,2-dioxide.

Another embodiment of the invention is the use of a purine as the alkylated nucleoside species. The common purine nucleosides are adenosine and guanosine. The alkylation of adenosine with a cyclic sulfate to give the 2' and 3'-O-ethylsulfonic acid sodium salts 17 and 18 is described in Example 9 (FIG. 9).

Figure 14:
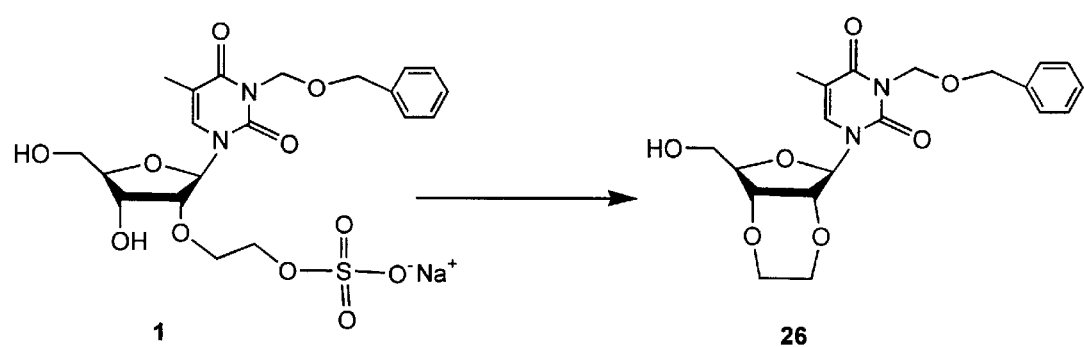
FIG. 14 Intramolecular reaction of 2'-O-(ethylsulfonic acid)sodium salt-N-3-(benzyloxy)methyl-5-methyluridine 1 with sodium methoxide in methanol.

Other nucleophiles useful in the invention for displacing the sulfate moiety includes alkoxides. Sodium methoxide in DMF as described in Example 10a (FIG. 10) is used to displace the sulfate moiety of 2'-O-ethylsulfonic acid sodium salt-N-3-(benzyloxy)methyl-5-methyluridine 1. Subsequent deprotection of the N-3-benzyloxymethyl group as described in Example 10b gives 20. Heating 2'-O-ethylsulfonic acid sodium salt-N-3-(benzyloxy)methyl-5-methyluridine 1 with sodium methoxide in methanol at 140° C. for 20 hours also gives a 28% yield of the cyclic 2',3'-O-ethylene-N-3-(benzyloxy)methyl-5-methyluridine 26 as described in Example 14 (FIG. 14).

Other nucleophilic species capable of displacing a sulfate moiety include but are not limited to sodium methoxide and other alkoxide species as well as hydroxyl amines and their salts generated by a strong base such as sodium hydride under anhydrous conditions. Subsequent nucleophilic displacement of the intermediate 2'-O-ethyl sulfonic acid or salts provides a route to the 2'-O-methoxyethyl and the 2'-O-aminooxy ethyl moieties, respectively.

While not wishing to be bound by theory, it is believed that the sulfate group can be further treated with a reactive organic species such as diazomethane or benzyl bromide or similar alkylating agents to give a sulfonate ester which has more electron withdrawing ability to render it a more facile leaving group for dislacement by a nucleophile.

As shown in Example 11 (FIG. 11), the use of a nucleophilic species such as sodium azide to displace the sulfate moiety of 2'-O-ethylsulfonic acid sodium salt-N-3-(benzyloxy)methyl-5-methyl uridine 1 upon heating at 80° C. gives the 2'-O-[2-(azido)ethyl]-N-3-(benzyloxy)methyl-5-methyluridine 21.

Alkylation of 2'-deoxy nucleosides and nucleotides are other embodiments of the invention. As shown in Examples 12a and 12b (FIG. 12), 5'-O-DMT-N-3-(benzyloxy)methyl-thymidine is alkylated at the 3'-hydroxyl position by treatment of the nucleoside with sodium hydride in DMF and addition of 1,3,2-dioxathiolane 2,2-dioxide to give the intermediate 3'-O-ethylsulfonic acid sodium salt-N-3-(benzyloxy)methyl-thymidine 22. Nucleophilic displacement of the sulfate moiety with sodium azide in DMF at 80° C. gives the 5'-O-DMT-3'-O-[2-(azido)ethyl]-N-3-(benzyloxy)methyl-thymidine 23. Also, as described in Examples 13a and 13b (FIG. 13), 3'-O-acetyl-N-(benzyloxy)methyl-thymidine is alkylated at the 5'-hydroxyl position under similar basic conditions using 1,3,2-dioxathiolane 2,2-dioxide as the alkylating agent. Nucleophilic displacement of the intermediate sulfate 24 with sodium azide in DMF at 80° C. gives 3'-O-acetyl-5'-O-[2-(azido)ethyl]-N-3-(benzyloxy)methyl-thymidine 25.

The anion of diethyl malonate is a potent carbon nucleophile. Nucleophilic displacement of the sulfate moiety of the 2'-O-ethylsulfonic acid sodium salt-N-3-(benzyloxy)methyl-5-methyluridine 1 intermediate with diethyl malonate is described in Example 15a and 15b. The diester 27 is hydrolyzed and is decarboxylated to give 2'-O-[4-(carboxy)propyl]-N-3-(benzyloxy)methyl-methyluridine 28.

The present invention provides improved methods for preparing nucleosides that are useful in the preparation of oligomeric compounds possessing superior hybridization properties. Structure-activity relationship studies have revealed that an increase in binding ($T_m$) of certain 2'-sugar modified oligonucleotides to an RNA target (complement) correlates with an increased "A" type conformation of the heteroduplex. Furthermore, absolute fidelity of the modified oligonucleotides is maintained. Increased binding of 2'-sugar modified sequence-specific oligonucleotides of the invention provides superior potency and specificity compared to phosphorus-modified oligonucleotides such as methyl phosphonates, phosphate triesters and phosphoramidates as known in the literature. Oligomeric compounds incorporating 2'-O-modified nucleosides of the invention are synthesized by standard solid phase nucleic acid synthesis using automated synthesizers such as Model 380B (Perkin-Elmer/Applied Biosystems) or MilliGen/Biosearch 7500 or 8800. Triester, phosphoramidite, or hydrogen phosphonate coupling chemistries are used with these synthesizers to provide the desired oligonucleotides (*Oligonucleotides: Antisense Inhibitors of Gene Expression.* M. Caruthers, 1989, 7, J. S. Cohen (Ed.), CRC Press, Boca Raton, Fla.). The Beaucage reagent (Beaucage et al., *J. Amer. Chem. Soc.*, 1990, 112, 1253) or elemental sulfur (Beaucage et al., *Tetrahedron Lett.*, 1981, 22, 1859) is used with phosphoramidite or hydrogen phosphonate chemistries to provide 2'-substituted phosphorothioate oligonucleotides.

In the context of the invention, the term "oligomeric compound" refers to a plurality of nucleoside monomers joined together in a specific sequence. The nucleosides of use in the present invention may be naturally-occurring or non-naturally occurring. Preferred nucleosides each have a nucleobase attached to a pentose sugar moiety and form oligomeric compounds via phosphorus linkages connecting the sugar moieties. Representative heterocyclic base moities, or nucleobases, include but are not limited to adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine.

2'-O-Modified nucleosides prepared according to the methods of the present invention can be further treated with reagents, using methods well known in the art and illustrated in the examples below, to convert the nucleosides into nucleoside surrogates. Nucleoside surrogates, such as DMT phosphoramidites shown in the examples below, are ready for use in standard oligonucleotide synthesis following well-established protocols. Nucleoside surrogates can include appropriate activated phosphorous atoms in $P^{III}$ or $P^V$ valence states for incorporation into an oligomeric compound. Such activated phosphorous atoms include phosphoramidites, hydrogen phosphonates and triesters. The nucleoside surrogates can also include appropriate hydroxyl blocking groups including, but not limited to, dimethoxytrityl, trimethoxytrityl, monomethoxytrityl and trityl blocking groups, and other blocking groups as are known in the art.

In positioning one of the nucleoside surrogate groups of the invention in an oligonucleotide, an appropriate blocked and activated nucleoside surrogate is incorporated in the oligonucleotides in the standard manler for incorporation of a normal blocked and active standard nucleotide. For instance, an 2'-O-nucleoside surrogate is selected that has an aminooxy moiety which is protected utilizing a phthalimido protecting group. One of the hydroxyl groups of the surrogate molecule is protected utilizing a dimethoxytrityl protecting group (a DMT protecting group) and the other hydroxyl group is present as a cyanoethoxy diisopropyl phosphoramidite moiety. The surrogate unit is added to the growing oligonucleotide by treating with the normal activating agents, as is known in the art, to react the phosphoramidite moiety with the growing oligomeric compound. This is followed by removal of the DMT group in the standard manner, as is known in the art, and continuation of elongation.

There are a number of modifications that can be made to nucleosides in combination with the 2'-O-modifications of the invention. Representative modifications that can be made to the sugar, base, or to the phosphate group of nucleosides are disclosed in International Publication Numbers WO 91/10671, published Jul. 25, 1991, WO 92/02258, published Feb. 20, 1992, WO 92/03568, published Mar. 5, 1992, and U.S. Pat. Nos. 5,138,045, 5,218,105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, and 5,587,469, all assigned to the assignee of this application. The disclosures of each of the above referenced publications are herein incorporated by reference.

The attachment of conjugate groups to oligonucleotides and analogs thereof is well documented in the art. Compounds of the present invention include compounds bearing conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Goups that enhance the pharmacokinetic properties, in the context ofthe present invention, include groups that improve oligomer uptake, distribution, metabolism or excretion. Representative conjugate groups are disclosed in International Patent Application PCT/US92/09196, filed Oct. 23,1992, U.S. Pat. No. 5,578,718, and U.S. Pat. No. 5,218,105. Each of the foregoing is commonly assigned with this application. The entire disclosure of each is incorporated herein by reference.

Cleavage of oligonucleotides by nucleolytic enzymes requires the formation of an enzyme-substrate complex or, in particular, a nuclease-oligonucleotide complex. The nuclease enzymes will generally require specific binding sites located on the oligonucleotides for appropriate attachment. If the oligonucleotide binding sites are removed or blocked, such that nucleases are unable to attach to the oligonucleotides, the oligonucleotides will be nuclease resistant. In the case of restriction endonucleases that cleave sequence-specific palindromic double-stranded DNA, certain binding sites such as the ring nitrogen in the 3- and 7-positions have been identified as required binding sites. Removal of one or more of these sites or sterically blocking approach of the nuclease to these particular positions within the oligonucleotide has provided various levels of resistance to specific nucleases.

Sugars having O-substitutions on the ribosyl ring are also amenable to the present invention. Representative substitutions for a ring oxygen include S, $CH_2$, CHF, and $CF_2$ (See, e.g., Secrist et al., Abstract 21, Program & Abstracts, Tenth International Roundtable, Nucleosides, Nucleotides and their Biological Applications, Park City, Utah, Sept. 16–20, 1992).

Nucleosides prepared by the methods of the present invention are useful in the preparation of oligomeric compounds which are utilized as diagnostics, therapeutics and as research reagents and kits. The oligomeric compounds can be utilized in pharmaceutical compositions by adding an effective amount to a suitable pharmaceutically acceptable diluent or carrier. The oligomeric compounds prepared according to the methods of the present invention can be used for treating organisms having a disease characterized by the undesired production of a protein. The organism can be contacted with an oligomeric compound which incorporates nucleosides prepared by the present methods. The oligomeric compound is synthesized to have a sequence that is capable of specifically hybridizing with a strand of target nucleic acid that codes for the undesirable protein.

EXAMPLES

General

All reagents and solvents are purchased from Aldrich Chemicals unless otherwise stated. Reactions are performed under an argon atmosphere unless otherwise noted. Column chromatography is carried out using normal phase silica gel. Solvent ratios are given as volume/volume. Solvent gradients are carried out step-wise. Evaporations of solvents are performed in vacuo (50 torr) at 35° C. unless otherwise specified. NMR spectra are obtained with the following instruments: $^1$H NMR: Varian Gemini-200 (199.975 MHZ) or Varian Unity 400 (399.952 MHZ). $^{13}$C NMR: Varian Gemini-200 (50.289 MHZ). $^{31}$P NMR: Varian Gemini-200 (79.990 MHZ). NMR spectra are recorded using either deuteriochloroform, dimethylsulfoxide-$d_6$dimethylformamide-$d_7$, or deuteriomethanol as solvent (tetramethylsilane as internal standard). The following abbreviations are used to designate the multiplicity of individual signals: s=singlet, d=doublet, t=triplet, q=quartet, m=multiplet, dd=doublet of doublets, br s=broad singlet. Mass spectra are performed by Mass Consortium, San Diego, Calif.

Example 1 (FIG. 1)

2'-O-(Ethylsulfonic acid) sodium salt-N-3-(benzyloxy)methyl-5-methyluridine (1)

N-3-(benzyloxy)methyl-5-methyluridine (41.57 g, 110 mmol) is dissolved in dry DMF (250 ml) and cooled to −45° C. NaH (4.8 g, 121 mmol) is added in three portions and the solution is warmed to 0° C. for one hour. The solution is cooled to −45° C. and solid 1,3,2-dioxathiolane 2,2-dioxide (15 g, 121 mmol) is added. The solution is allowed to warm to room temperature. The solution is checked by TLC in 5 hours which showed the reaction to be complete. The solvent is removed in vacuo and the residue is purified by silica gel column chromatography. The residue is applied to a column of silica gel and the product is eluted with a gradient of 5% to 10% methanol in dichloromethane. The appropriate fractions are collected and evaporated in vacuo to give 25.60 g (44%) of the title compound 1, isolated as its sulfonic acid. The sulfates are produced in a 4 to 1 ratio as the 2' and 3' alkylated products 1 and 2 (2D $^1$H NMR TOCSY is used to characterize the 2' alkylation). $^1$H NMR (DMSO-d6): 1.81(s, 3H, 5-methyl)., 3.55–3.78(m, 6H, 2XCH2, 5'5"H's), 3.88(m 3.96(m, 1H, 2'H), 4.13(m, 1H, 3'H), 4.59(s, 2H, methylene), 5.08(d, 1H, 3'OH), 5.10(t, 1H, 5'OH), 5.36(s, 2H, methylene), 5.84(d, 1H, 1'H), 7.28(m, 5H, benzyl), 7.93(d, 1H, 6H). ESMS [M-H]-: m/e 501.2 found, calculated 501.49.

Figure 2:
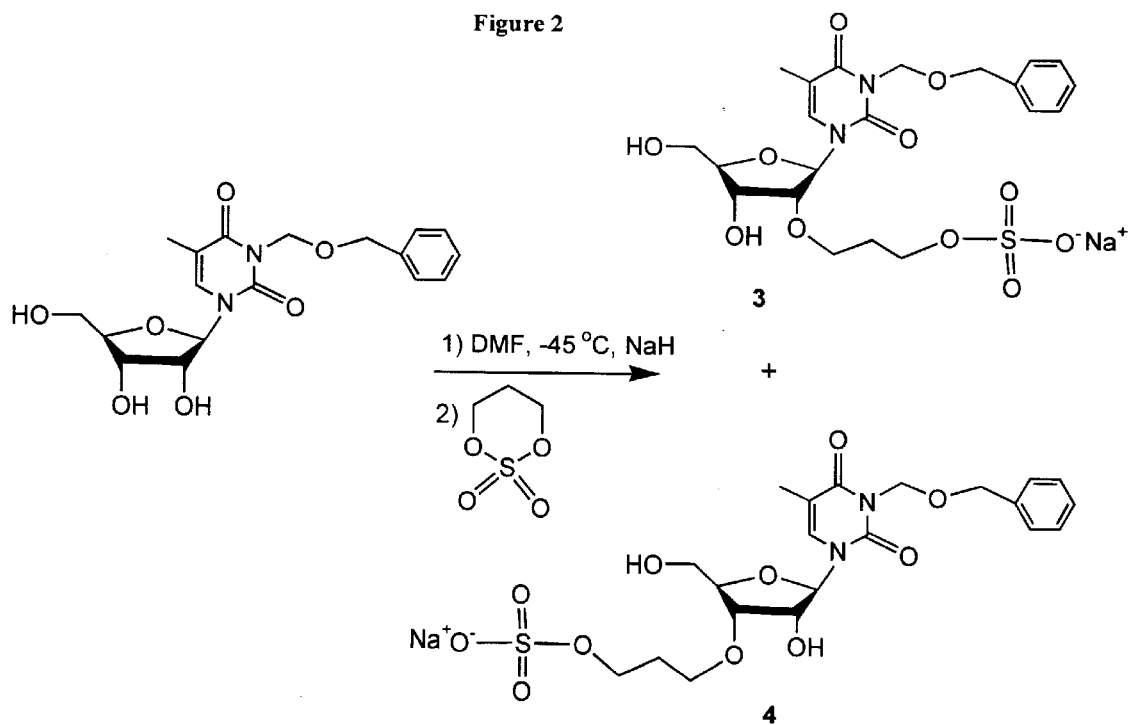
FIG. 2 Alkylation of N-3-(benzyloxy)methyl-5-methyluridine with 1,3-propanediol cyclic sulfate (1,3,2-dioxathiane 2,2-dioxide).

Example 2 (FIG. 2)

2'-O-(Propylsulfonic acid) sodium salt-N-3-(benzyloxy) methyl-5-methyluridine (3)

N3-(benzyloxy)methyl-5-methyluridine (15.00 g, 39.6 mmol) is dissolved in dry DMF (90 ml) and cooled to −45° C. NaH (2.38 g, 59.5 mm) is added in three portions and the solution is allowed to warm to 0° C. for one hour. The solution is cooled to −45° C. and solid 1,3-propanediol cyclic sulfate (1,3,2-dioxathiane 2,2-dioxide)(8.2 g, 59.9 mmol) is added. The solution is allowed to warm to room temperature. The solution is checked by TLC in 5 hours which showed the reaction to be complete. The solvent is removed in vacuo and the residue is purified by silica gel column chromatography. The residue is applied to a column of silica gel and the product is eluted with a gradient of 5% to 10% methanol in dichloromethane which contains 1–2% of triethylamine. The appropriate fractions are collected and evaporated in vacuo to give 10.21 g (42%) of the title compound 3 isolated as its triethylamine salt. The sulfates are produced in a 4 to 1 ratio of the 2' to 3' alkylated products 3 and 4. 1H NMR (CDCl3): 1.33(t, methyl of triethylamine), 1.95(bs, 5H, CH3 of base and CH2 of propyl), 3.06(q, methylene of triethylamine), 3.82 (m, 4H), 4.05(m, 4H), 4.33(m, 2H), 4.65(s, 2H, CH2), 5.46(s, CH2), 5.78(d, 1H, 1'H), 7.28(m, 5H, benzyl), 7.64(s, 1H, 6H). ESMS [M−H]−: m/e calculated 515.52, found 515.10.

Figure 3:
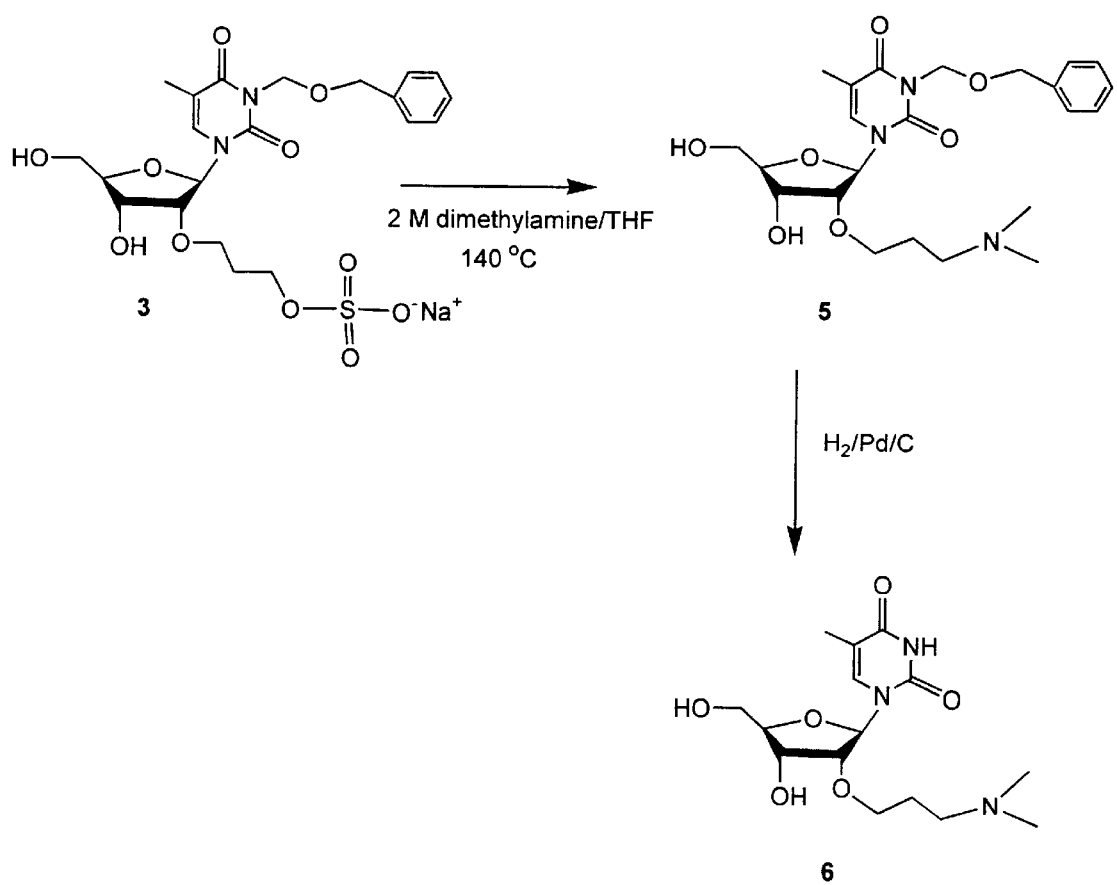
FIG. 3 Nucleophilic displacement of 2'-O-propylsulfonic acid sodium salt-N-3-(benzyloxy)methyl 5-methyluridine 3 with dimethylamine and deprotection of 2'-O-(N,N-dimethyl-propyl)-N-3-(benxyloxy)methyl-5-methyluridine 5 by a catalytic hydrogenation.

Example 3a (FIG. 3)

2'-O-(N,N-Dimethylpropyl)-N-3-(benxyloxy) methyl-5-methyluridine (5)

2'-O-Propylsulfonic acid sodium salt-N-3-(benzyloxy) methyl-5-methyluridine 3,(10.20 g, 16.54 mmol) is dissolved in 2M dimethylamine in THF and is placed in a stainless bomb. The bomb is sealed and heated at 140° C. for 20 hours. After cooling, the TLC showed the reaction to be complete. The solvent is evaporated in vacuo and the residue is purified by silica gel chromatography using a 15% methanol, 35% ethyl acetate and 50% dichloromethane. The appropriate fractions are collected and evaporated in vacuo to give 2.77 g (36%) of the title compound 5. 1H NMR (CDCl3): 1.92(bs, 5H, CH3, CH2), 2.81(s, 6H, dimethylamine), 3.10(m, 1H), 3.33 (m, 1H), 3.80–4.09(m, 6H, 2',4',5',5" & CH2), 4.53(t, 1H, 3'H), 4.64(s, 2H, CH2), 5.42(s, 2H, CH2), 5.87(d, 1H, 1'H), 7.28(m, 5H, benzyl), 7.64(s, 1H, 6H). ESMS [M+H]+: m/e calculated 464.53, found 464.00.

Example 3b (FIG. 3)

2'-O-[2-(N,N-dimethyl)aminopropyl]-5-methyluridine (6)

2'-O-(N,N-dimethylpropyl)-N-3-(benxyloxy)methyl-5-methyluridine 5(0.9 g, 1.94 mmol) is dissolved in absolute ethanol (70 mL) and glacial acetic acid (20 mL) and is added to a Parr bottle. Palladium hydroxide (0.18 g, 20 wt %) is added and the bottle is charged with 50 psi of hydrogen and is shakened on a Parr hydrogenator apparatus for several hours until the starting material disappeared (TLC, CH$_2$Cl$_2$: MeOH: NH$_4$OH, 8.7:1:3). The reaction mixture is filtered through Celite and the filtrate is concentrated in vacuo to give 0.45 g (67%) of the title compound 6. $^1$H NMR (200 MHz, DMSO-d6) d: 1.74 (bm, 2H), 1.83 (s, 3H), 2.27(s, 6H), 2.46(m, 2H), 3.64(m, 4H), 3.89(m, 2H), 4.22(t, 1H), 5.23(bs, 1H), 5.89(d,1H), 7.85(s,1H), 10.23(bs,NH). $^{13}$C NMR (50 MHz, DMSO) d: 12.50, 27.86, 36.59, 57.71, 62.04, 70.01, 70.23, 83.40, 86.50, 88.79, 111.51, 138.19, 152.50. ESMS m/z 344 (M+H)$^+$.

Figure 4:
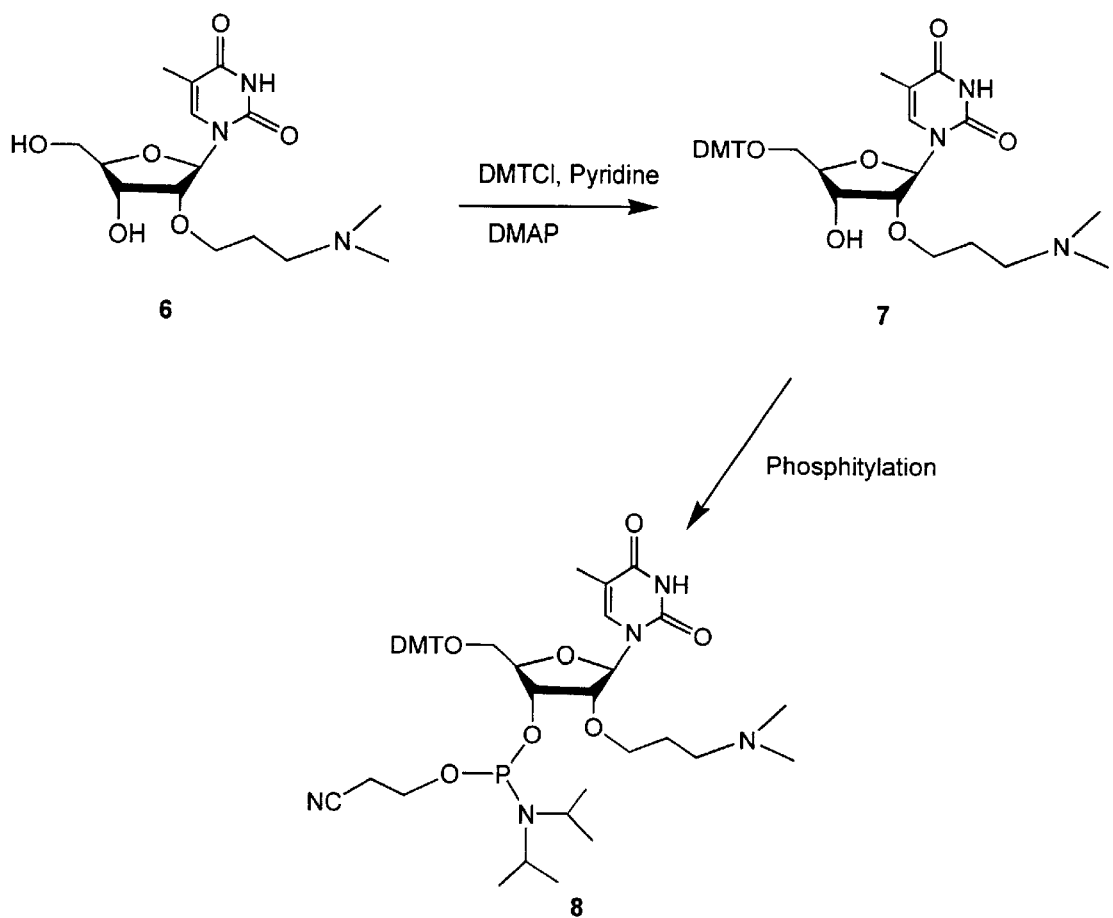
FIG. 4 Protection ofthe 5'-hydroxyl of 2'-O-[2-(N,N-dimethyl)aminopropyl]-5-methyluridine 6 with 4,4'-dimethoxytrityl chloride (DMTCl) and phosphitylation of 5'-O-DMT-2'-O-[2-(N,N-dimethyl)aminopropyl]-5-methyluridine 7.

Example 4a (FIG. 4)

5'-O-DMT-2'-[2-(N,N-dimethyl)aminopropyl]-5-methyluridine (7)

2'-O-[2-(N,N-dimethyl)aminopropyl]-5-methyluridine 6 (0.22 g, 0.64 mmol) is dried in vacuo overnight and is co-evaporated with pyridine (10 mL) and the residue is dissolved in anhydrous pyridine (30 mL). To this solution, dimethylamino pyridine (0.015 g, 7% by wt.) and 4,4'-dimethoxytrityl chloride (DMTCl) (0.26 g, 0.77 mmol) is added and the reaction mixture is stirred at room temperature under an argon atmosphere for several hours until the TLC (CH$_2$Cl$_2$:MeOH:Et$_3$N, 9.3:5:2) showed all the starting material disappeared. The reaction is quenched by addition of methanol (0.5 mL) and the solvent is removed in vacuo. The residue is purified by silica gel column chromatography by elution with 5% triethylamine in ethylacetate to give 0.30 g (73%) of the title compound 7. $^1$H NMR (200 MHz, CDCl$_3$) d: 1.36 (s, 3H), 1.68 (bm, 1H), 1.95 (bm,1H), 2.22 (s, 6H), 2.35 (bm, 1H), 2.59(bm, 1H), 3.29–3.65 (m, 3H), 3.79 (s, 6H), 3.93 (m, 1H), 4.04 (m, 2H), 4.45 (t, 1H), 6.08 (d, 1H), 6.08 (d, 1H), 6.86 (d, 4H), 7.205 (m, 1H), 7.60 (s, 1H). $^{13}$C NMR (200 MHz, CDCl$_3$) d: 12.29, 26.81, 45.45, 55.82, 57.35, 63.76, 69.26, 70.39, 82.65, 84.73, 87.46, 87.75, 111.52, 113.81, 127.68, 128.26, 128.55, 128.81, 130.74, 135.98, 136.13, 136.31, 145.01, 151.12, 159.28, 164.63, 228.37.

Example 4b (FIG. 4)

5'-O-DMT-2'-O-[2-(N,N-dimethyl)aminopropyl]-5-methyluridine-3'-O-[(2-cyanoethyl)N,N-diiopropyl] phosphoramidite (8)

5'-O-DMT-2'-O-[2-(N,N-dimethyl)aminopropyl]-5-methyluridine 7 (0.71 g, 0.94 mmol) is mixed with N,N-diisopropylamine tetrazolide (0.08 g, 0.47 mmol) and dried over anhydrous P$_2$O$_5$ in vacuo. Anhydrous dichloromethane (10 mL) is added followed by the addition of 2-cyanoethyl N,N,N'N'-tetraisopropylphosphorodiamidite (0.45 mL, 1.41 mmol) and the reaction mixture is stirred at room temperature under argon atmosphere overnight. The reaction mixture is diluted with dichloromethane (30 mL) and is washed with 5% NaHCO$_3$ solution (25 mL) and brine (25 mL). The organic phase is dried over anhydrous MgSO$_4$, filtered and is evaporated to dryness in vacuo. The residue is purified by silica gel column chromatography by elution with ethyl acetate to give 0.45 g (51%) of the title compound 8 as a foam. $^{31}$P NMR (200 Mhz, CDCl$_3$) d: 150.90, 151.43.

Example 5a (FIG. 5)

5'-O-DMT-2'-O-[3-(N,N-dimethyl)aminopropyl]-3'-O-succinyl-5-methyluridine (9)

5'-O-DMT-2'-O-[2-(N,N-dimethyl)aminopropyl]-5-methyluridine 7 (0.20 g, 0.31 mmol) is mixed with succinic anhydride (0.69 g, 0.69 mmol) and 4-(dimethylamino) pyridine (0.019 g, 0.16 mmol). The mixture is dried over P$_2$O$_5$ overnight in vacuo. The residue is diluted with dichloromethane (0.9 mL) and triethylamine (0.14 mL, 1.01 mmol). The reaction mixture is stirred at room temperature for 6 h. The solvent is removed in vacuo and the residue is purified by silica gel column chromatography by elution with a solution of dichloromethane:methanol:triethylamine, (8.7:1:0.3) to give 0.20 g (85%) of the title compound 9 as a foam. R$_f$=0.33 (CH$_2$Cl$_2$: MeOH: triethylamine, 8.7:1:0.3). $^1$H NMR (200 MHz, CDCl$_3$) dd 1.08 (t, 9H, J=7.18 Hz), 1.4 (s, 3H), 1.92 (m, 2H), 2.54 (s, 6H), 2.62 (m, 10H), 2.91 (m, 1H), 3.37–3.74 (m, 5H), 3.61 (s, 6H), 4.29 (t, 2H, J=4.52 Hz), 5.38 (t, 1H, J=5.48 Hz), 6.05 (d, 1H, J=4.5 Hz), 6.85 (d, 4H, J=8.78 Hz), 7.26–7.42 (m, 9H, 7.62 (s, 1H); $^{13}$C NMR (50 MHz, CDCl$_3$) dd 9.08, 11.05, 26.39, 30.35, 31.34, 43.73, 44.66, 54.86, 55.07, 62.20, 68.80, 70.28, 80.06, 80.99, 86.47, 86.7, 110.91, 112.94, 126.82, 127.39, 127.69, 129.75, 134.86, 143.82, 150.65, 158.36, 164.18, 172.64, 177.32; MS (FAB) m/z 746 (M+H)+.

Example 5b (FIG. 5)

5'-O-DMT-2'-O-[3-(N,N-dimethyl)aminopropyl]-5-methyluridine-3'-O-succinyl CPG (10)

5'-O-DMT-2'-O-[3-(N,N-dimethyl)aminopropyl]-3'-O-succinyl-5-methyluridine 9 (0.19 g, 0.25 mmol) is dried over $P_2O_5$ in vacuo at 40° C. overnight. Anhydrous DMF (0.62 mL) is added followed by addition of 2-(1H-benzotriazole)-1-yl)-1,1,3,3-tetramethyluronium tetrafluoroborate (0.081 g, 0.25 mmol) and N-methylmorpholine (55 mmL, 0.5 mmol). The reaction mixture is vortexed for several minutes to give a clear solution and anhydrous DMF (2.4 mL) and activated CPG (1.08 g, 1 15.2 mmol/g, particle size 120/200, mean pore diameter 520 Å) are added. The mixture is allowed to shake on a shaker for 18 h. An aliquot is withdrawn and the loading capacity is estimated. The functionalized CPG is filtered and washed thoroughly with DMF, $CH_3CN$ and $Et_2O$ and dried in vacuo overnight. The functionalized CPG 10 is added to a capping solution (2 mL of Cap A, acetic anhydride/lutidine/THF; 2 mL of Cap B, N-methylimidazole/THF, Perspective Biosystems Inc.) and allowed to shake on a shaker for 2 h. The CPG 10 is filtered and washed with $CH_3CN$, $Et_2O$ and dried in vacuo. The loading capacity of CPG 10 is determined by standard procedure and the final loading is 52.62 μmol/g.

Example 5c

Synthesis of oligonucleotides containing the 2'-O-[3-(N,N-dimethy)aminopropyl] modification The phosphoramidite 8 is dissolved in anhydrous acetonitrile to give a 0.1 M solution which is loaded on to an Expedite Nucleic Acid Synthesis system (Millipore 8909) to synthesize the oligonucleotides. The coupling efficiencies were more than 98%. For the coupling of the modified phosphoramidite 8, the coupling time is extended to 10 minutes and this step is carried out twice. All other steps in the protocol supplied by Millipore are used as such. After completion of the synthesis, the CPG is suspended in aqueous ammonia (30 wt %) and kept at room temperature for 2 h to deprotect the oligonucleotides form the CPG. The CPG is filtered and the filterate is heated at 55° C. for 6 h to complete the deprotection of all protecting groups. The filtrate is evaporated to half the volume on a speed vacuum concentrator and subjected to purification by High Performance Liquid Chromatography (HPLC, Waters, C-4, 7.8× 300 mm, A=50 mM triethylammonium acetate, pH=7, B=acetonitrile, 5 to 60% B in 55 Min, Flow 2.5 mL/min., ll=260 nm). Detritylation with aqueous 80% acetic acid and evaporation followed by desalting by HPLC on Waters C-4 column gives the 2'-modified oligonucleotides (Table 1). Oligonucleotides are analyzed by HPLC, CGE and mass spectrometry.

TABLE 1

Oligonucleotides Containing 2'-o-[3-(N,N-dimethyl)aminopropyl] Modification

| SEQ ID # | ISIS # | Sequence | Mass Calc. | Mass Obs. | HPLC Rtt Time (min.[a]) |
|---|---|---|---|---|---|
| 23 | 111710 | 5' T*CC AGG T*GT* CCG CAT*C 3' | 5239.36 | 5237.6 | 16.85 |
| 24 | 111709 | 5' CTC GTA CT*T* T*T*C CGG TCC 3' | 5797.85 | 5796.80 | 17.58 |
| 25 | 111711 | 5' GCGT*T*T*T*T*T* T*T*T* T*GCG 3' | 5887.34 | 5886.40 | 16.90 |

T* = 2'-O-[3-(N,N-dimethyl)aminopropyl]$^{5Me}$U
[a]Waters C-4, 3.9 × 300 mm, solvent A = 50 mm TEAAc, pH 7; Solvent B = $CH_3CN$; gradient 5–60% B in 55 min; flow rate 1.5 mL/min, 1 = 260 nm

TABLE 2

Tm Values of 2'-O-[3-(N,N-dimethyl)aminopropyl] Modifications

| SEQ ID # | ISIS # | Sequence 5'-3' | Target RNA ° C. | ΔTmC | Dtm/mod. ° C. |
|---|---|---|---|---|---|
| 26 | 2221 | TCC AGG TGT CCG CAT C | 62.3 | | |
| | | T*CC AGG T*GT* CCG CAT* C | 66.94 | 4.64 | 1.16 |
| 27 | 3404 | GCG TTTTTTTTT GCG | 48.3 | | |
| | 111711 | GCGT*T*T*T*T*T*T*T*T*GCG | 46.5 | -1.8 | -0.18 |
| 28 | 2896 | CTC GTA CTT TTC CGG TCC | 61.8 | | |
| | 111709 | CTC GTA CT*T* T*T*C CGG TCC | 61.88 | 0.08 | 0.02 |

T* = 2'-O-[3-(N,N-dimethyl)aminopropyl]$^{5Me}$U

Figure 6:
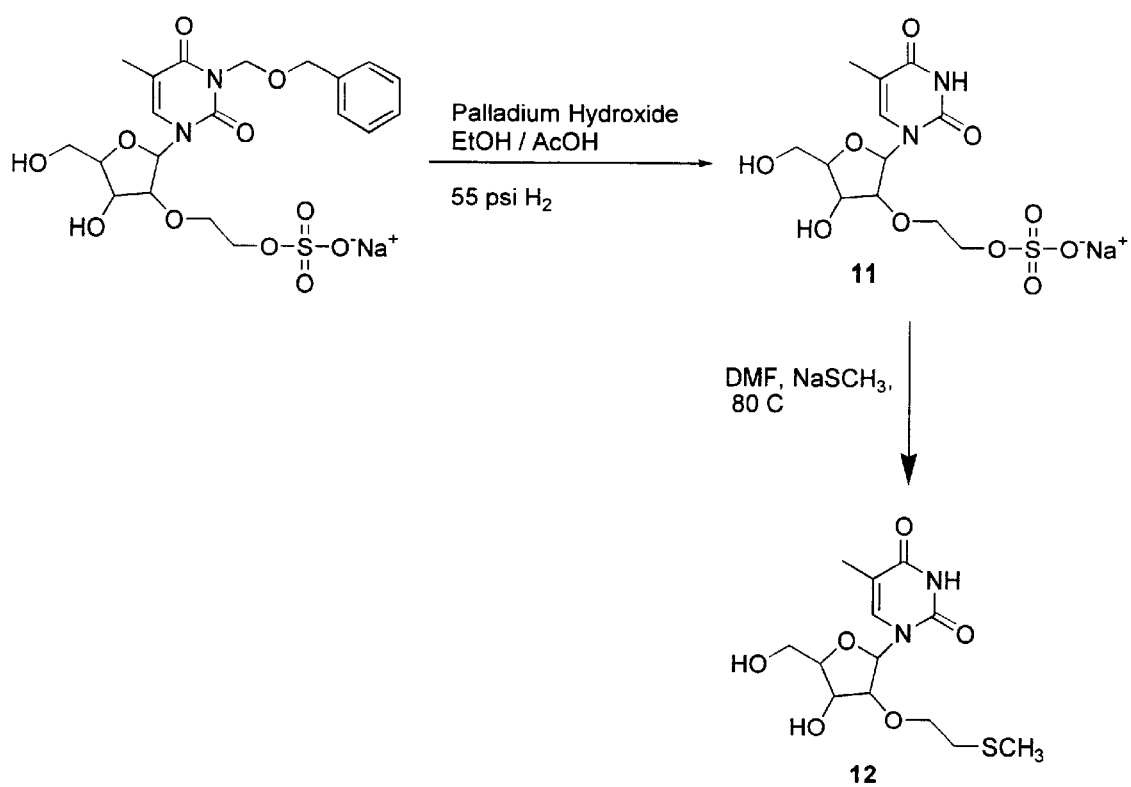
FIG. 6 Deprotection of 2'-O-ethylsulfonic acid sodium salt-N-3-(benzyloxy)methyl-5-methyluridine 1 by a catalytic hydrogenation and nucleophilic displacement of 2'-O-(ethylsufonic acid) sodium salt-5-methyluridine 11 with sodium thiomethoxide.

Example 6a (FIG. 6)

2'-O-(Ethylsulfonic acid) sodium salt-5-methyluridine (11)

2'-O-Ethylsulfonic acid sodium salt-N-3-(benzyloxy) methyl-5-methyluridine 1 (5 g, 9.53 mM) is dissolved in a mixture of EtOH and AcOH (30 ml/30ml). To this mixture was added palladium hydroxide (1 g). The reaction is placed on a Parr hydrogenation apparatus at 55 psi of $H_2$ overnight. The reaction is complete by TLC (20% MeOH in dichloromethane). The solution is filtered through a bed of celite and evaporated in vacuo until dry. The product 11 is not purified further.

Example 6b (FIG. 6)

2'-O-[2-(thiomethyl)ethyl]-5-methyluridine (12)

2'-O-(Ethylsufonic acid) sodium salt-5-methyluridine 11 (3.64 g, 9.53 mM, amount based on 100% conversion to compound 1) is dissolved in 70 ml DMF and sodium thiomethoxide (6.68 g, 95.3 mM) is added as a solid. The reaction mixture is heated at 80° C. overnight. The reaction is complete by TLC (10% MeOH in dichloro-methane). The reaction mixture is poured into water and extracted with ethyl acetate. The organic phase is washed with brine, dried over anhydrous $MgSO_4$, filtered and evaporated to dryness. The residue is purified by silica gel column chromatography by elution with ethyl acetate to give 0.24 g (56 %) of the title compound 12. $^1$H NMR (200 Mhz, $CDCl_3$) d: 1.92 (s, 3H), 2.15 (s, 3H), 2.69 (m, 3H), 3.20 (d, 2H), 3.64–3.88 (m, 2H), 4.05(s, 3H), 4.21(t, 1H), 4.35 (t, 1H), 4.71 (s, 2H), 5.49 (s, 2H), 5.65 (d, 111), 7.28 (m, 4H), 7.45 (s,1H). MS (HRFAB$^+$) (Mna$^+$) m/z Cal. 475.1515, found 475.1510.

Example 7a (FIG. 7)

5'-O-DMT-2'-O-methylthioethyl-5-methyluridine

2'-O-methylthioethyl-5-methyluridine 12 (3.16 g, 9.53 mmol)is dissolved in pyridine (40ml) and solid 4,4'-dimethoxy-tritylchloride (DMTCl) (3.23 g, 9.53 mmol) is added in one portion and the mixture is stirred overnight. The reaction is complete by TLC (40% EtOAc in dichloromethane). The reaction is partitioned between ethyl acetate and water (70 ml EtOAc/50 ml $H_2O$). The aqueous layer was extracted twice with EtOAc (25 ml each). The combined organic layers are washed with water (30 ml), brine (30 ml) and dried over $MgSO_4$. The mixture is filtered and the solvent is evaporated in vacuo to give a yellow residue. The residue is purified by silica gel column chromatography and is eluted with 30% ethyl acetate in dichloromethane. The appropriate fractions are collected and concentrated in vacuo to afford 2.05 g (34%) of the title compound 13. $^1$H NMR ($CDCl_3$) d: 1.42 (s, 3H), 2.03 (s, 3H), 2.74 (m, 2H), 3.13 (d, 1H), 3.46 (dd, 2H), 3.81 (bs, 7H), 4.13 (m 2H), 5.97 (d, 1H)<6.83 (d, 4H), 7.29 (m, 9H), 7.68 (s, 1H), 8.92 (bs, NH).

Example 7b (FIG. 7)

5'-O-DMT-2'-O-[2-(thiomethyl)ethyl]-5-methyluridine-3'-O-[(2-cyanoethyl)N,N-diiopropyl] phosphoramidite (14)

5'-O-DMT-2'-O-methylthioethyl-5-methyluridine 13 (1 g, 1.58 mM) is dissolved in dry dichloromethane (30 ml). To this solution is added; tetrazolide salt (297 mg, 1.73 mM) and 2-cyanoethyl N,N,N'N'-tetraisopropylphosphorodiamidite (600 mL, 1.89 mM) is added dropwise to the reaction mixture. The reaction is complete by TLC (25% EtOAc in dichloromethane) after 20 hrs. The reaction is partitioned between EtOAc and saturated sodium bicarbonate (50 ml/50 ml). The organic layer is washed with brine, dried over $MgSO_4$, filtered and concentrated to a yellow foam. The product is purified by silica gel chromatography (25% EtOAc in dichloromethane). The appropriate fractions are collected and dried in vacuo. The residue is dissolved in a minimal amount of dry dichloromethane (5 ml) and 300 ml of hexane is added. The solvent is decanted from the precipitate. The white residue is then dried on the roto-evaporater and on high vacuum over $P_2O_5$ to give 1.10 g (83% yield) of title compound 14.

$^{31}$P NMR (200 Mhz, $CDCl_3$) δ: 151.17, 151.32

Example 8a and 8b (FIG. 8)

5'-O-DMT-2'-O-[2-(thiomethyl)ethyl]-5-methyluridine-3'-O-succinyl CPG (16)

Compound 13 is converted into the 3'-succinyl derivative 15 by treatment with succinic anhydride in presence of dimethylamino pyridine and triethylamine in $CH_2Cl_2$. This is then attached to CPG in presence of coupling reagents to give functionalized CPG 16.

Example 9 (FIG. 9)

2'-O-(Ethylsulfonic acid) sodium salt-adenosine (17)

Compounds 17 and 18 are synthesized starting from adenosine using similar reaction conditions as used for the synthesis of compound 1 and 2.

Figure 10:
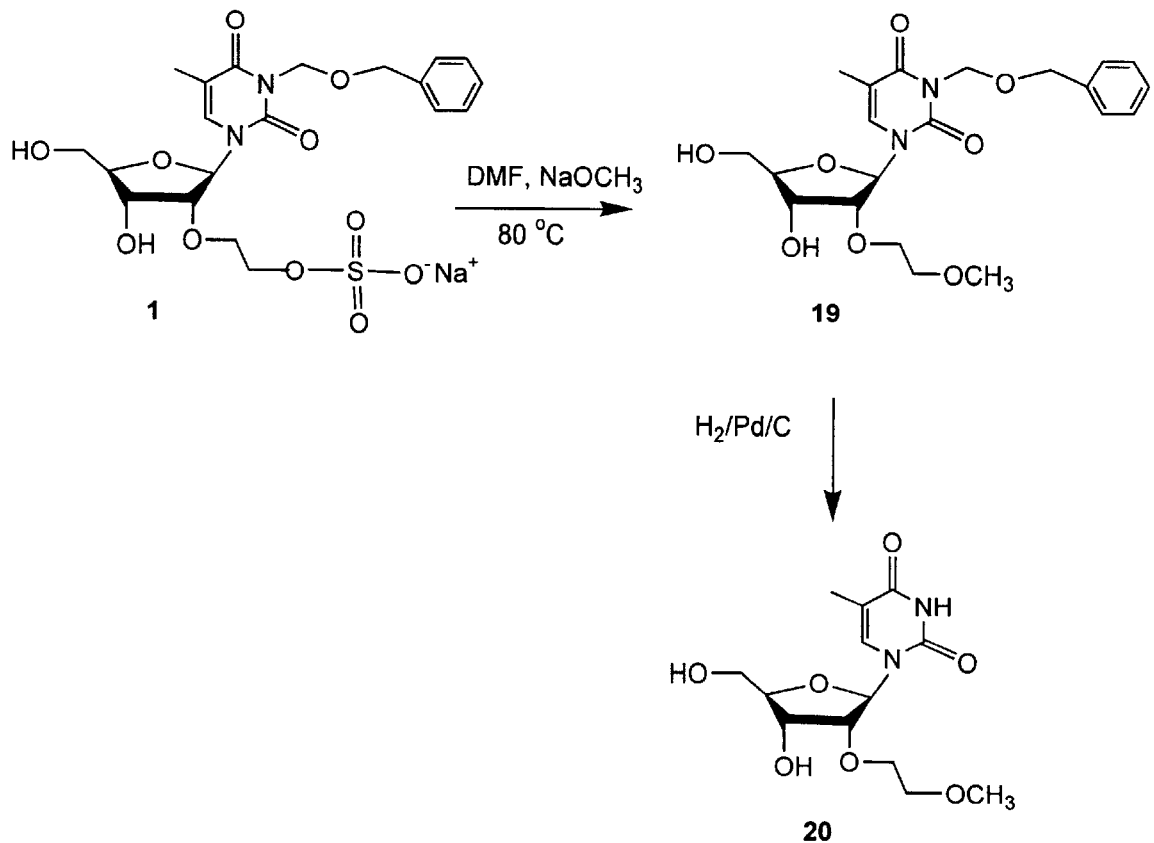
FIG. 10 Nucleophilic displacement of 2'-O-(ethylsulfonic acid) sodium salt-N-3-(benzyloxy)methyl-5-methyluridine 1 with sodium methoxide in DMF and deprotection of 2'-O-[2-(methoxy) ethyl]-N-3-(benxyloxy)methyl-5-methyluridine 5 by a catalytic hydrogenation.

Examples 10a and 10b (FIG. 10)

2'-O-[2-(methoxy)ethyl]-5-methyluridine (20)

2'-O-Ethylsulfonic acid sodium salt-N-3-(benzyloxy) methyl-5-methyluridine 1 is heated with $NaOCH_3$ in DMF at 80° C. to give compound 19. Hydrogenation with Pd/C as the catalyst removes the N-3 benzyloxy protecting group to give compound 20.

Figure 11:
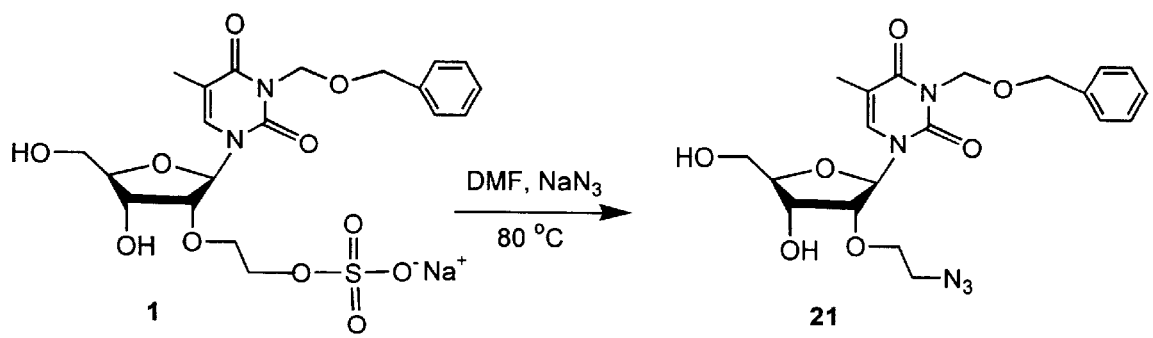
FIG. 11 Nucleophilic displacement of 2'-O-(ethylsulfonic acid) sodium salt-N-3-(benzyloxy)methyl-5-methyluridine 1 with sodium azide.

Example 11 (FIG. 11)

2'-O-[2-(azido)ethyl]-N-3-(benzyloxy)methyl-5-methyluridine (21)

2'-O-Ethylsulfonic acid sodium salt-N-3-(benzyloxy) methyl-5-methyluridine 1 is heated with $NaN_3$ in DMF at 80° C. to give compound 21.

Figure 12:
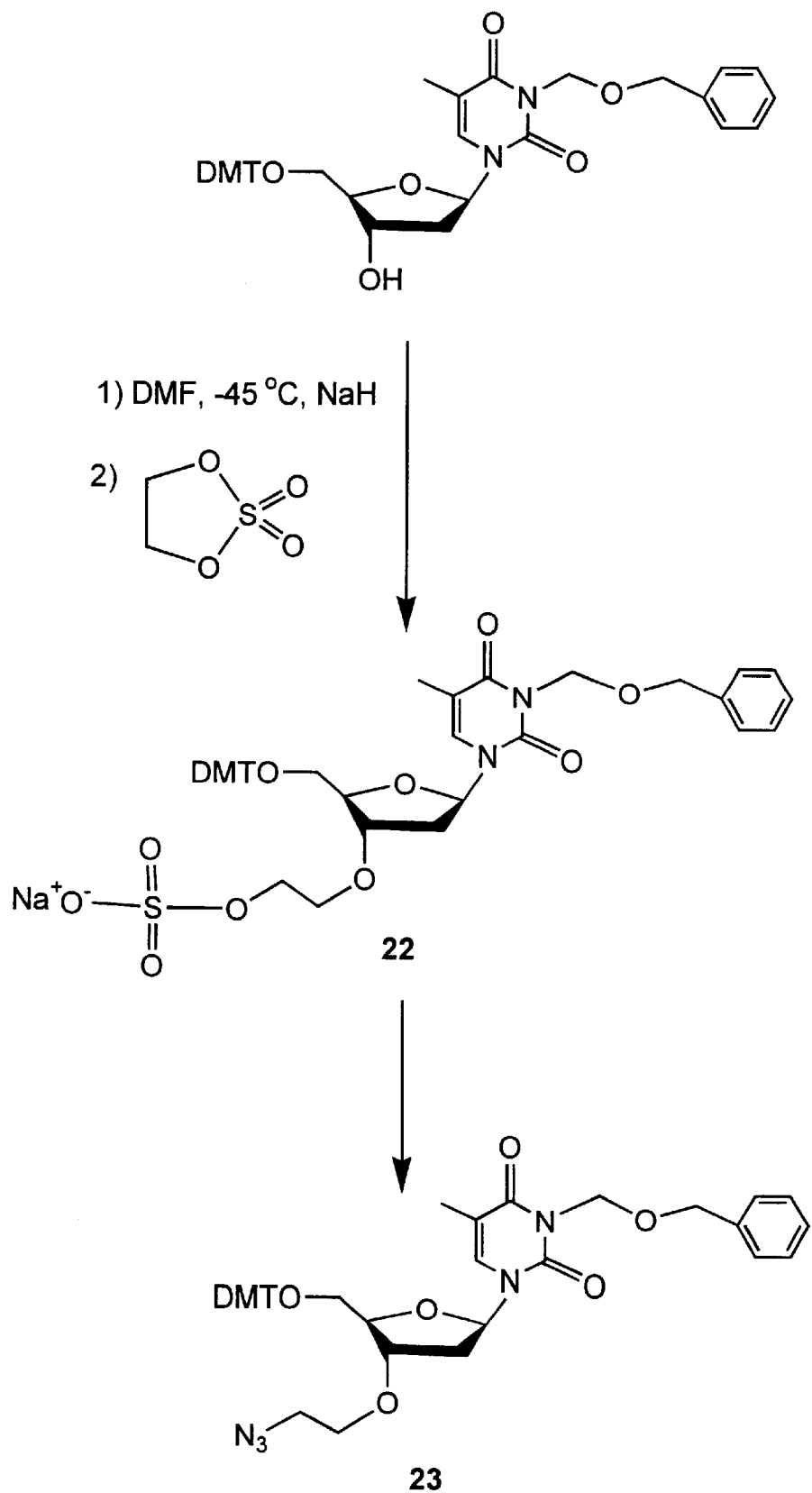
FIG. 12 Alkylation of 5'-O-DMT-N-3-(benzyloxy) methyl-thymidine with 1,3,2-dioxathiolane 2,2-dioxide and nucleophilic displacement of 5'-O-DMT-3'-(ethylsulfonic acid)sodium salt-N-3-(benzyloxy)methyl-thymidine 22 with sodium azide.

Examples 12a and 12b (FIG. 12)

3'-O-[2-(azido)ethyl]-N-3-(benzyloxy)methyl-5'-O-DMT-thymidine (23)

5'-O-DMT-N-3-(benzyloxy)methyl-thymidine is treated with NaH in DMF at −40° C. Addition of 1,3,2-dioxathiolane 2,2-dioxide to the reaction mixture gives compound 22. This is then heated with $NaN_3$ in DMF at 80° C. to give compound 23.

Figure 13:
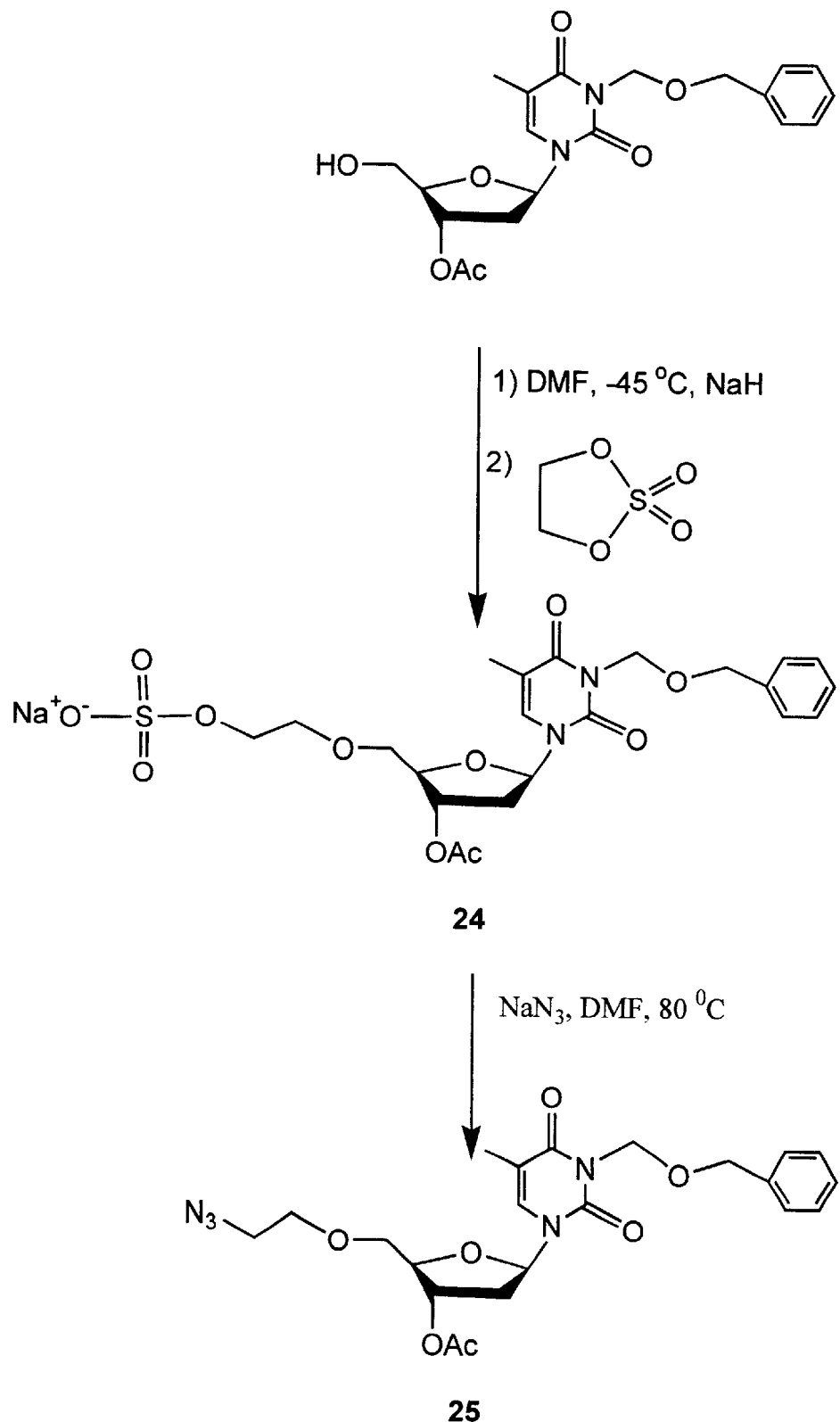
FIG. 13 Alkylation of 3'-O-acetyl-N-3-(benzyloxy) methyl-thymidine with 1,3,2-dioxathiolane 2,2-dioxide and nucleophilic displacement of 3 '-O-Acetyl-5'-O-[(ethylsulfonic acid) sodium salt]-N-3-(benzyloxy)methyl-thymidine 24 with sodium azide.

Example 13 (FIG. 13)

3'-O-Acetyl-5'-O-[2-(azido)ethyl]-N-3-(benzyloxy) methyl-thymidine (25)

3'-O-Acetyl-N-3-(benzyloxy)methyl-thymidine is treated with NaH in DMF and is reacted with 1,3,2-dioxathiolane 2,2-dioxide to give compound 24. This is converted into compound 25 by heating with NaN₃ in DMF at 80° C.

Example 14 (FIG. 14)

2',3'-O-ethylene-N-3-(benzyloxy)methyl-5-methyluridine (26)

2'-O-Ethylsulfonic acid sodium salt-N-3-(benzyloxy)-methyl-5-methyluridine 1(0.5 g, 0.95 mmol) is dissolved in methanol in a steel bomb. Sodium methoxide (0.08 g, 1.45 mmol) is added and the bomb is sealed and heated at 140° C. for 20 h. The methanol is evaporated in vacuo and the residue is purified by silica gel column chromatography by elution with ethyl acetate to give 0.11 g (28%) of the title compound 26.

Figure 15:
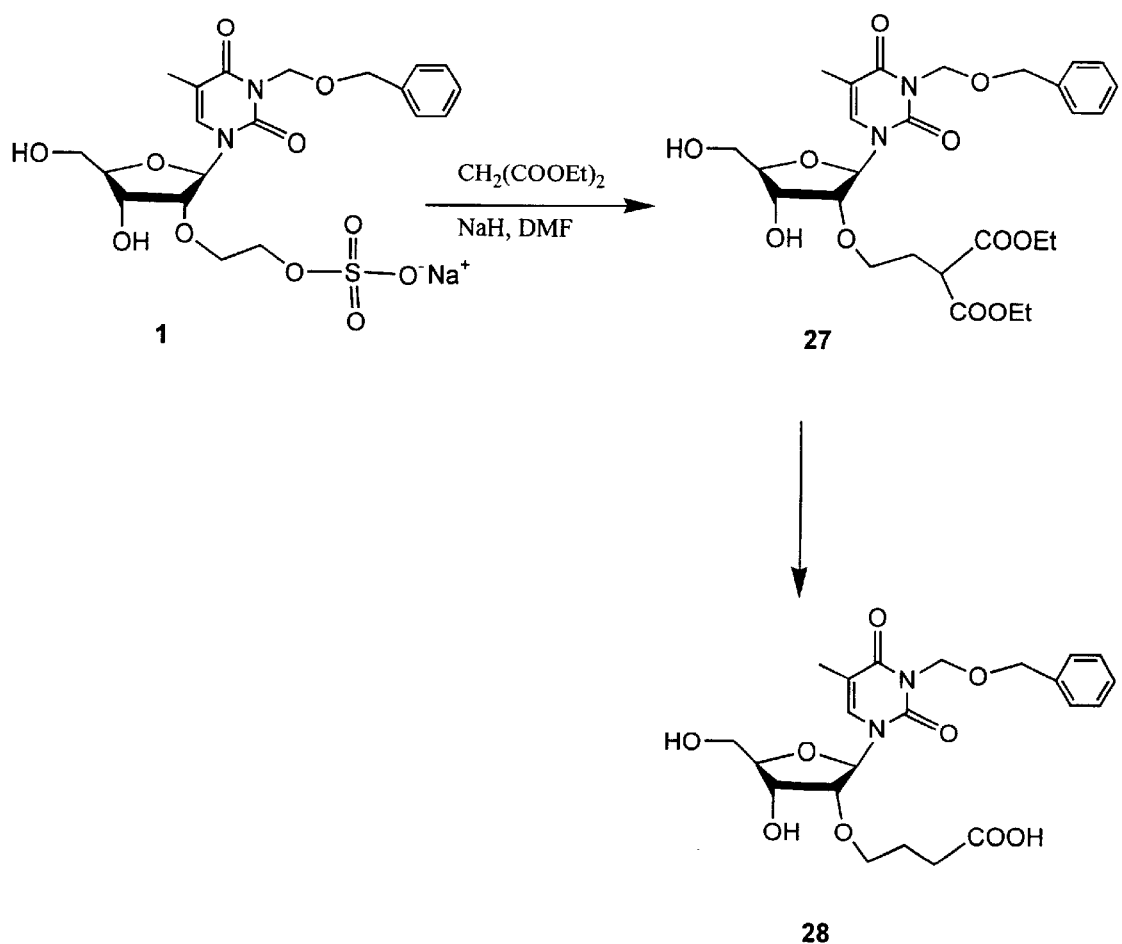
FIG. 15 Nucleophilic displacement of 2'-O-(ethylsulfonic acid)sodium salt-N-3-(benzyloxy)methyl-5-methyluridine 1 with diethylmalonate.

Example 15a and 15b (FIG. 15)

2'-O-[4-(carboxy)propyl]-N-3-(benzyloxy)methyl-5-methyluridine (28)

Compound 1 is treated with a mixture of NaH and diethyl malonate in DMF to give compound 27 which is then converted into compound 28.

PROCEDURE 1

Control of ICAM-1 Expression

Oligonucleotide Treatment of HUVECs: Cells are washed three times with Opti-MEM (Life Technologies, Inc.) pre-warmed to 37C. The oligonucleotides are premixed with 10 g/mL Lipofectin (Life Technologies, Inc.) in Opti-MEM, serially diluted to the desired concentrations, and applied to washed cells. Basal and untreated (no oligonucleotide) control cells are also treated with Lipofectin. Cells are incubated for 4 h at 37° C., at which time the medium is removed and replaced with standard growth medium with or without 5 mg/mL TNF-α 7 & D Systems. Incubation at 37° C. is continued until the indicated times.

Quantitation of ICAM-1 Protein Expression by Fluorescence-activated Cell Sorter Cells are removed from plate surfaces by brief trypsinization with 0.25% trypsin in PBS. Trypsin activity is quenched with a solution of 2% bovine serum albumin and 0.2% sodium azide in PBS (+Mg/Ca). Cells are pelleted by centrifugation (1000 rpm, Beckman GPR centrifuge), resuspended in PBS, and stained with $31/10^5$ cells of the ICAM-1 specific antibody, CD54-PE (Pharmingin). Antibodies are incubated with the cells for 30 min at 4° C. in the dark under gentle agitation. Cells are washed by centrifugation procedures and then resuspended in 0.3 mL of FacsFlow buffer (Becton Dickinson) with 0.5% formaldehyde (Polysciences). Expression of cell surface ICAM-1 is then determined by flow cytometry using a Becton Dickinson FACScan. Percentage of the control ICAM-1 expression is calculated as follows: [(oligonucleotide-treated ICAM-1 value)—(basal ICAM-1 value)/(non-treated ICAM-1 value)—(basal ICAM-1 value)]. (Baker, Brenda, el. al. 2'-O-(2-Methoxy)ethyl-modified Anti-intercellular Adhesion Molecule 1 (ICAM-1) Oligonucleotides Selectively Increase the ICAM-1 mRNA leved Inhibit Formation ofthe ICAM-1 Translation Initiation Complex in Human Umbilical Vein Endothelial Cells, *The Journal of Biological Chemistry*, 1997, 272, 11994). ICAM-1 expression of 2'-O-(2-methyl-thioethyl) modified oligonucleotides of the invention is measured by the reduction of ICAM-1 levels in treated HUVEC cells. The oligonucleotides are believed to work by a direct binding RNase H independent mechanism. Appropriate scrambled control oligonucleotides are used as controls. They have the same base composition as the test sequence.

Sequences that contain the 2'-O-(2-methyl-thioethyl) modification as listed in Table 3 below are prepared and tested in the above assay. SEQ ID NO: 3, a C-raf targeted oligonucleotide, was used as a control in measuring ICAM-1 expression.

TABLE 3

Oligonucleotides Containing 2=-O-(2-methyl-thioethyl) modification

| SEQ ID NO: | Sequence (5'-3') | Target |
|---|---|---|
| 1 | 5'-$T_sC^m_sT_sG_sA_sG_sT_sA_sG_sC^m_s$ $A_sG_sA_sG_sG_sA_sG_sC^m_sT_sC$-3' | Human ICAM-1 |
| 2 | 5'-$T_oC^m_oT_oG_oA_oG_oT_oA_oG_oC^m_o$ $A_oG_oA_oG_oG_oA_oG_oC^m_oT_oC$-3' | Human ICAM-1 |
| 3 | 5'-$A_sT_sG_sC^m_sT_sA_sT_sC_s{}^mT_sG_sC_s{}^mC_s{}^mC_s{}^mC_s{}^m$ $C^m_sA_sA_sG_sG_sA$-3' | mouse C-raf |
| 4 | 5'-$G_sC^m_sC^m_sC^m_sA_sA_sG_sC^m_sT_sG_sG_sC^m_s$ $A_sT_sC^m_sC^m_sG_sT_sC^m_sA$-3' | Human ICAM-1 |

All nucleosides in bold are 2=-O-(2-methyl-thioethyl); subscript S indicates a phosphorothioate linkage; subscript O indicates a phosphodiester linkage; and superscript m on C($C^m$) indicates a 5-methyl-C.

PROCEDURE 2

Enzymatic Degradation of 2'-O-Modified Oligonucleotides

Three oligonucleotides are synthesized incorporating the modifications shown in Table 4 below at the 3'-end. These modified oligonucleotides are subjected to snake venom phosphodiesterase action.

Oligonucleotides (30 nanomoles) are dissolved in 20 mL of buffer containing 50 mM Tris-HCl pH 8.5, 14 mM $MgCl_2$, and 72 mM NaCl. To this solution 0.1 units of snake-venom phosphodiesterase (Pharmacia, Piscataway, N.J.), 23 units of nuclease P1 (Gibco LBRL, Gaithersberg, Md.), and 24 units of calf intestinal phosphatase (Boehringer Mannheim, Indianapolis, Ind.) are added and the reaction mixture is incubated at 37° C. for 100 hours. HPLC analysis is carried out using a Waters model 715 automatic injector, model 600E pump, model 991 detector, and an Alltech (Alltech Associates, Inc., Deerfield, Ill.) nucleoside/nucleotide column (4.6×250 mm). All analyses are performed at room temperature. The solvents used are A: water and B: acetonitrile. Analysis of the nucleoside composition is accomplished with the following gradient: 0–5 min., 2% B (isocratic); 5–20 min., 2% B to 10% B (linear); 20–40 min., 10% B to 50% B. The integrated area per nanomole is determined using nucleoside standards. Relative nucleoside ratios are calculated by converting integrated areas to molar values and comparing all values to thymidine, which is set at its expected value for each oligomer. The assay reveals the nuclease resistance of the modified oligomers.

TABLE 4

Relative Nuclease Resistance of 2'-Modified
Chimeric Oligonucleotides
5'-TTT TTT TTT TTT TTT T*T*T*T*-3' SEQ ID NO:5
(Uniform phosphodiester)

| T* = 2'-modified T | Modification |
|---|---|
| —O—CH$_2$—CH$_2$—S—CH$_3$ | MTE (methyl thioethyl) |
| —O—CH$_2$—CH$_2$—O—CH$_3$ | MOE (methoxyethoxy) |
| —O—CH$_2$—CH$_2$—CH$_2$—N(CH$_3$)$_2$ | DMAP (dimethylaminopropyl) |

PROCEDURE 3

General Procedure for the Evaluation of Gapped 2'-o-mte and 2'-o-dmap Modified Oligonucleotides Targeted to Ha-ras Different types of human tumors, including sarcomas, neuroblastomas, leukemias and lymphomas, contain active oncogenes of the ras gene family. Ha-ras is a family of small molecular weight GTPases whose function is to regulate cellular proliferation and differentiation by transmitting signals resulting in constitutive activation of ras are associated with a high percentage of diverse human cancers. Thus, ras represents an attractive target for anticancer therapeutic strategies.

SEQ ID NO: 6 is a 20-base phosphorothioate oligodeoxynucleotide targeting the initiation of translation region of human Ha-ras and it is a potent isotype-specific inhibitor of Ha-ras in cell culture based on screening assays (IC$_{50}$=45 nm). Treatment of cells in vitro with SEQ ID NO: 6 results in a rapid reduction of Ha-ras mRNA and protein synthesis and inhibition of proliferation of cells containing an activating Ha-ras mutation. When administered at doses of 25 mg/kg or lower by daily intraperitoneal injection (IP), SEQ ID NO: 6 exhibits potent antitumor activity in a variety of tumor xenograft models, whereas mismatch controls do not display antitumor activity. SEQ ID NO: 6 has been shown to be active against a variety of tumor types, including lung, breast, bladder, and pancreas in mouse xenograft studies (Cowsert, L. M. *Anti-Cancer Drug Design*, 1997, 12, 359). A second-generation analog of SEQ ID NO: 6, where the 5' and 3' termini ("wings") of the sequence are modified with 2'-methoxyethyl (MOE) modification and the backbone is kept as phosphorothioate (Table 2, SEQ ID NO: 12), exhibits IC$_{50}$ of 15 nm in cell culture assays. A 3-fold improvement in efficacy is observed from this chimeric analog. Because of the improved nuclease resistance and binding affinity of the 2'-MOE phosphorothioate, SEQ ID NO: 12 increases the duration of antisense effect in vitro. This will relate to frequency of administration of this drug to cancer patients. SEQ ID NO: 12 is currently under evaluation n ras dependent tumor models (Cowsert, L. M. *Anti-Cancer Drug Design*, 1997, 12, 359). The parent compound, SEQ ID NO: 6, is in Phase I clinical trials against solid tumors by systemic infusion. Antisense oligonucleotides having the 2'-O-MTE and 2'-O-DMAP (dimethylaminopropyl) modifications are prepared and tested in the aforementioned assays in the manner described to determine activity.

TABLE 5

Ha-ras Antisense Oligonucleotides with 2'-o-mte and 2'-o-dmap
Modifications and Their Controls

| SEQ ID # | Sequence | Backbone | 2'-Modif. | Comments |
|---|---|---|---|---|
| 6 | 5'-TsCsCs GsTsCs AsTsCs Gs CsTs CsCsTs CsAsGs GsG-3' | P=S | 2'-H | parent |
| 7 | 5'-TsCsAs GsTsAs AsTsAs Gs GsCs CsCsAs CsAsTs GsG-3' | P=S | 2'-H | mismatch control |
| 8 | 5'-ToToCo <u>GsTsCs AsTsCs Gs CsTs</u> CoCoTo CoAoGo GoG-3' | P=O/ P=S/ P=O | 2=-O-MTE in the wings | Gapmer (mixed backbone) |
| 9 | 5'-TsCsCs <u>GsTsCs AsTsCs Gs CsTs</u> CsCsTs CsAsGs GsG-3' | P=S | 2'-O-MTE in the wings | Gapmer as uniform thioate |
| 10 | 5'-ToCoAo <u>GsTsAs AsTsAs GsCsCs GsCsCs Gs</u> Co Co CoAo CoAoTo GoG-3' | P=O/ P=S/ P=O | 2=-O- DMAP in the wings | Gapmer (mixed backbone) |
| 11 | 5'-TsCsAs <u>GsTsAs AsTs As GsCsCs</u> GsCsCs CsCsAs CsAsTs GsC-3' | P=S | 2=-O- DMAP in the wings | Gapmer as uniform thioate |
| 12 | 5'-TsCsCs <u>GsTsCs AsTsCs Gs CsTs</u> CsCsTs CsAsGs GsG-3' | P=S | 2'-MOE in the wings | Gapmer with MOE as control |

TABLE 5-continued

Ha-ras Antisense Oligonucleotides with 2'-o-mte and 2'-o-dmap Modifications and Their Controls

| SEQ ID # | Sequence | Backbone | 2'-Modif. | Comments |
|---|---|---|---|---|
| 13 | 5'-TsCsAs<u>GsTsAs AsTsAsGsCs CsGsCsCsCsAsCsAsTs</u> GsC-3' | P=S | 2'-MOE in the wings | Gapmer with MOE as control | underlined portions of sequences are 2'-deoxy

PROCEDURE 4

General Procedure for the Evaluation of 2'-o-dmap Oligonucleotides Targeted to HCV Uniformly modified 2'-O-DMAP phosphodiester oligonucleotides are evaluated for antisense inhibition of HCV gene via a translation arrest mechanism. Hepatitis C virus (HCV) is known to be responsible for liver disease in many millions of people throughout the world. HCV is an enveloped, positive-strand RNA virus of the flavivirus family. Initial infections in humans are typically asymptomatic, but chronic infection often ensues in which liver cirrhosis and hepatocellular carcinoma are long-term sequella. Interferon-α (IFN-α) therapy is widely used in attempts to eradicate the virus from chronically infected individuals, but long-term remissions are achieved in only about 20% of patients, even after 6 months of therapy. So far, there is no antiviral drug available for the treatment of HCV. (Blair et al., 1998). Drug discovery and development efforts have been hampered by the lack of suitable cell culture replication assays for HCV, and vaccine production has been hampered by genetic variability of the virus' envelope genes. Specific inhibitors of cloned viral enzymes such as proteases and the viral polymerase have not yet been reported.

Antisense oligonucleotide therapy represents a novel approach to the control of HCV infection. Several antisense oligonucleotides complementary to HCV RNA sequences adjacent to the polyprotein initiation codon of HCV have been designed at Isis (Hanecak et al., J. Virol., 1996, 70, 5203). The target genome is highly conserved among independent HCV isolates.

It was shown that an RNase H-independent antisense oligonucleotide had greater activity than its parent phosphorothioate (which will work by RNase H mechanism) which was targeted to the AUG site of a core protein sequence of HCV in a human hepatocyte cell line employing a uniformly modified 2'-O-(methoxyethyl) phosphodiester (P=O 20 mer) (Hanecak et al., J. Virol., 1996, 70, 5203, Hanecak et al., J. Virol., 1996, 70, 5203). Hepatitis C virus core protein levels were reduced as efficiently as the corresponding 2'-deoxyphosphorothioate with an $IC_{50}$ of 100 nm. SEQ ID NO: 15 was a potent inhibitor of core protein expression without affecting HCV RNA levels. This suggested the inhibition of HCV translation. The parent compound (SEQ ID NO: 14) had Tm of 50.8C while the 2'-MOE compound (SEQ ID NO: 15) had a Tm of 83.8C. Thus, SEQ ID NO: 15 had a better affinity for HCV RNA. The replicative cycle of HCV takes place in the cytoplasm of infected cells, in which RNase H levels have been reported to reduce relative to those of the nucleus. For this reason, it is better to utilize an antisense oligonucleotide which will work by non-RNase H mechanism to inhibit HCV. Oligonucleotide SEQ ID NO: 15 is an attractive lead since it contains a P=O linkage with a 2'-MOE modification. SEQ ID NO: 16 will be tested in accordance with the testing of SEQ ID NO: 14 and 15.

TABLE 6

5'-TTT AGG ATT CGT GCT CAT GG-3'
Antisense Oligonucleotide Targeting HCVC 5'-NCR
Nucleotide Numbers 340–359

| SEQ ID NO: | Backbone | 2'-modification | Tm (C) |
|---|---|---|---|
| 14 | P=S | 2'-deoxy | 50.8 |
| 15 | P=O | 2'-MOE | 83.8 |
| 16 | P=O | 2'-O-DMAP | |

PROCEDURE 5

In Vitro Assays

Isis antisense oligonucleotides complementary to the HCV polyprotein initiation codon sequence are known to inhibit expression of the viral core protein in immortalized cell lines engineered to express HCV RNA from recombinant DNA integrated into the host cell genome (Hanecak et al., J. Virol., 1996, 70, 5203). Non-complementary control oligonucleotides have no effect on HCV RNA or protein levels in this system. H8Ad17° C. cells will be treated with a range of concentration of oligonucleotides shown in Table 5 above (0–200 nm) in the presence of cationic lipids and total protein levels will be evaluated 20 hours later by western blot analysis.

PROCEDURE 6

In Vivo Model for HCV

Animal models of HCV infection are not readily available. An alternative approach has been developed to evaluate antisense oligonucleotides to inhibit HCV gene expression in livers of mice. For these experiments, HCV sequences, including SEQ ID NO: 15 target sequence, were fused to a luciferase reporter gene and inserted into a Vaccinia virus. Infection of mice with this recombinant vaccination virus results in quantifiable levels of luciferase in liver tissue. Potent phosphorothioate antisense oligonucleotides have been shown to work in this model. SEQ ID NO: 16 (the 2=-O-DMAP RNA analog of SEQ ID NO: 15) will be evaluated for inhibition of expression of the HCV-luciferase construct in livers of mice infected with the recombinant vaccinia virus. Inhibition will be evaluated for sequence-dependency and dose response. HCV-luciferase expression in livers of mice infected with a control vaccinia virus vector lacking HCV target sequences will be used as control and the effect of antisense drug in these control systems will be evaluated. (Antisense oligonucleotide-mediated inhibition of hepatitis C virus gene expression in mouse liver (Anderson et al., Meeting Abstracts, International Hepatitis Meeting, Hawaii, 1997).

PROCEDURE 7

In Vivo Nuclease Resistance

The in vivo Nuclease Resistance of gapmers having the 2=-O-DMAP is studied in mouse plasma and tissues (kidney and liver). For this purpose, the C-raf oligonucleotide series SEQ ID NO: 17 is used and the following five oligonucleotides listed in Table 5 below evaluated for their relative nuclease resistance.

TABLE 7

| SEQ ID NO: | Sequence | Backbone | Description |
|---|---|---|---|
| 17 | 5'-ATG CAT TCT GCC CCA AGGA-3' | P=S, 2'-H | (control) rodent C-raf antisense oligo |
| 18 | *AoToGoCoA*sTsTsCsTsGsCsCsCs Cs*AoAoGoGoA* | P=O/ P=S/ P=O | (control) 2'-*MOE*/2'-H/*2'-MOE* |
| 19 | *AsTsGsCsAs*TsTsCsTsGsCsCsCsC s*AsAsGsGsA* | P=S | (control) 2'-MOE/2'-H/ 2'-MOE |
| 20 | *AoToGoCoA*sTsTsCsTsGsCsCsCs Cs*AoAoGoGoA* | P=O/ P=S/ P=O | 2'-O-DMAP/ 2'-H/ 2'-O-DMAP |
| 21 | *AsTsGsCsAs*TsTsCsTsGsCsCsCs | P=S | 2'-O-DMAP/ |

TABLE 7-continued

| SEQ ID NO: | Sequence | Backbone | Description |
|---|---|---|---|
| | Cs*AsAsGsGsA* | | 2'-H/ 2'-O-DMAP |

PROCEDURE 8

Animal Studies

For each oligonucleotide to be studied, 9 male BALB/c mice (Charles River, Wilmington, Mass.), weighing about 25 g are used (Crooke et al., *J. Pharmacol. Exp. Ther.*, 1996, 277, 923). Following a 1-week acclimation, the mice receive a single tail vein injection of oligonucleotide (5 mg/kg) administered in phosphate buffered saline (PBS), pH 7.0. The final concentration of oligonucleotide in the dosing solution is (5 mg/kg) for the PBS formulations. One retro-orbital bleed (either 0.25, 9.05, 2 or 4 post dose) and a terminal bleed (either 1, 3, 8 or 24 h post dose) is collected from each group. The terminal bleed (approximately 0.6–0.8 mL) is collected by cardiac puncture following ketamine/xylazine anesthesia. The blood is transferred to an EDTA-coated collection tube and centrifuged to obtain plasma. At termination, the liver and kidneys will be collected from each mouse. Plasma and tissues homogenates will be used for analysis for determination of intact oligonucleotide content by CGE. All samples will be immediately frozen on dry ice after collection and stored at −80° C. until analysis.

What is claimed is:

1. A process for preparing a compound of the formula I,

wherein:

A is a carbohydrate, oligonucleotide, nucleotide, or nucleoside;

X is a O, S, or N;

$R_1$ and $R_2$ are independently H, alkyl, aryl, O-alkyl, O-aryl, carboxylic acid, amide, ester, halogen, trifluoromethyl, or amine;

n is 2–10; and,

Y is H, Li, Na, K, Cs or an amine;

comprising the steps of:

treating a compound of formula II,

A—X—H     (II)

with a compound of formula III:

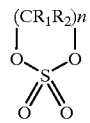     (III)

to give said compound of formula I.

2. The process of claim 1 wherein A is a purine or a pyrimidine β-D-ribofuranosyl nucleoside or a purine or a pyrimidine β-D-2'-deoxyribofuranosyl nucleoside.

3. The process of claim 1 wherein said treating step comprises reacting the compounds in solution.

4. The process of claim 3 wherein said solution is in aprotic solvent.

5. The process of claim 4 wherein said aprotic solvent is acetonitrile, dimethylacetamide, dimethylformamide, dimethyl-sulfoxide or tetrahydrofuran.

6. The process of claim 3 wherein said treating step includes cooling said solution from about 0° C. to about −78° C.

7. The process of claim 6 wherein said treating step includes treating said cooled solution with a base.

8. The process of claim 7 wherein said base is a metal hydride, hydroxide or carbonate.

9. The process of claim 7 wherein said base is sodium hydride, potassium hydride, lithium hydride, sodium hydroxide, potassium hydroxide, lithium hydroxide, sodium carbonate, potassium carbonate or cesium carbonate.

10. The process of claim 7 wherein said base is sodium hydride.

11. The process of claim 7 wherein said treating step includes warming the cooled, base treated solution from about −78° C. to about 0° C.

12. The process of claim 11 wherein said warming step takes place over a period of from about 5 minutes to about 60 minutes.

13. The process of claim 12 wherein said treating step includes cooling said warmed base treated solution from about 0° C. to about −78° C.

14. The process of claim 7 wherein said treating step includes reacting said base treated solution with a cyclic sulfate.

15. The process of claim 14 wherein said cyclic sulfate is substituted with alkyl, aryl, O-alkyl, O-aryl, carboxylic acid, amide, ester, halogen, trifluoromethyl, or amine.

16. The process of claim 14 wherein said cyclic sulfate is a five membered ring.

17. The process of claim 14 wherein said cyclic sulfate is a six membered ring.

18. The process of claim 14 wherein said reacted solution is warmed from about 0° C. to about 30° C.

19. The process of claim 18 wherein said reacted solution is warmed over a time period of from about 1 hour to about 24 hours.

20. A process for preparing a compound of formula IV

A—X—(CR$_1$R$_2$)$_n$—Z     (IV)

wherein:

A is a carbohydrate, an oligonucleotide, a nucleotide, or a nucleoside;

X is a O, S, or N;

R$_1$ and R$_2$ are independently H, alkyl, aryl, O-alkyl, O-aryl, carboxylic acid, amide, ester, halogen, trifluoromethyl, or amine;

n is 2–10; and,

Z is H, amine, azide, halogen, thiol, O-alkyl, O-aryl, alkyl, aryl;

comprising the steps of:

providing a compound of formula II;

A—X—H     (II)

and treating said compound with a compound of formula III:

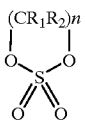     (III)

to give an intermediate compound of the formula:

A—X—(CR$_1$R$_2$)$_n$—O—SO$_2$—O$^-$Y$^+$ wherein Y is H,Li,Na,K,Cs or an amine; and, reacting the resulting compound with a nucleophile to provide the compound having formula IV.

21. The process of claim 20 wherein said intermediate compound is reacted with the nucleophile at a temperature of from about 0° C. to about 200° C.

22. The process of claim 20 wherein said intermediate compound is reacted with the nucleophile over a time period of from about 1 hour to about 24 hours.

23. The process of claim 20 wherein said nucleophile is an amine.

24. The process of claim 23 wherein said nucleophile is dimethylamine.

25. The process of claim 20 wherein said nucleophile is an alkoxide.

26. The process of claim 25 wherein said nucleophile is sodium methoxide.

27. The process of claim 20 wherein said nucleophile is a thiol.

28. The process of claim 27 wherein said nucleophile is sodium thiomethoxide.

29. A compound of formula I:

A—X—(CR$_1$R$_2$)$_n$—O—SO$_2$—O$^-$Y$^+$     (I)

wherein:

A is a carbohydrate, an oligonucleotide, a nucleotide, or a nucleoside;

X is a O, S, or N;

R$_1$ and R$_2$ are independently H, alkyl, aryl, O-alkyl, O-aryl, carboxylic acid, amide, ester, halogen, trifluoromethyl, or amine;

n is 2–10; and,

Y is H,Li,Na,K,Cs or an amine.

30. The compound of the formula I of claim 29 wherein A is a purine or a pyrimidine β-D-ribofuranosyl nucleoside or a purine or a pyrimidine β-D-2'-deoxyribofuranosyl nucleoside.

31. A process for preparing a compound of formula VI,

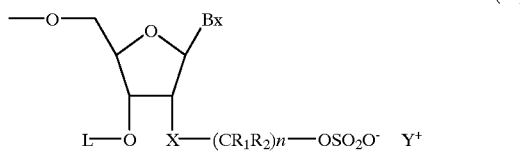

(VI)

wherein:
Bx is a heterocyclic base moiety;
Q is H or a hydroxyl protecting group;
L is H or a hydroxyl protecting group;
X is O, N or S;
$R_1$ and $R_2$ are independently H, alkyl, aryl, O-alkyl, O-aryl, carboxylic acid, amide, ester, halogen, trifluoromethyl, or amine;
n is 2–10; and,
Y is H,Li,Na,K,Cs or an amine;
comprising the steps of:
providing a compound of formula V,

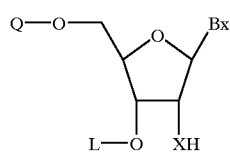

(V)

and treating the compound of formula V with a compound of formula III

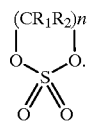

32. The process of claim 31 wherein Bx is a purine or a pyrimidine base optionally substituted with a protecting group.

33. The process of claim 31 wherein said treating step includes reacting said compound of formula V in solution.

34. The process of claim 33 wherein said solution is in an aprotic solvent.

35. The process of claim 34 wherein said aprotic solvent is acetonitrile, dimethylacetamide, dimethylformamide, dimethyl-sulfoxide or tetrahydrofuran.

36. The process of claim 33 wherein said treating step includes cooling said solution from about 0° C. to about −78° C.

37. The process of claim 33 wherein said treating step includes treating said cooled solution with a base.

38. The process of claim 37 wherein said base is a metal hydride, hydroxide or carbonate.

39. The process of claim 37 wherein said base is sodium hydride, potassium hydride, lithium hydride, sodium hydroxide, potassium hydroxide, lithium hydroxide, sodium carbonate, potassium carbonate or cesium carbonate.

40. The process of claim 37 wherein said base is sodium hydride.

41. The process of claim 37 wherein said treating step includes warming said cooled base treated solution from about −78° C. to about 0° C.

42. The process of claim 41 wherein said warming step is over a period of from about 5 minutes to about 60 minutes.

43. The process of claim 41 wherein said treating step includes cooling said warmed base treated solution from about 0° C. to about −78° C.

44. The process of claim 37 wherein said treating step includes reacting said base treated solution with a cyclic sulfate.

45. The process of claim 44 wherein said cyclic sulfate is substituted with alkyl, aryl, O-alkyl, O-aryl, carboxylic acid, amide, ester, halogen, trifluoromethyl, or amine.

46. The process of claim 45 wherein said cyclic sulfate is a five membered ring.

47. The process of claim 45 wherein said cyclic sulfate is a six membered ring.

48. The process of claim 41 wherein said reacted solution is warmed from about 0° C. to about 30° C.

49. The process of claim 48 wherein said warmed takes place over a period of from about 1 hour to about 24 hours.

50. A process for preparing a compound of the formula VII,

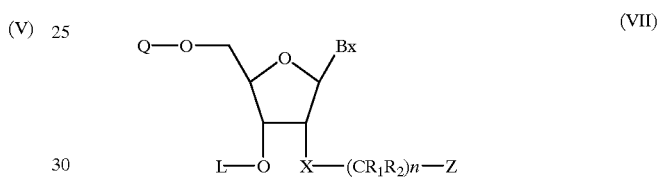

(VII)

wherein:
Bx is a heterocyclic base moiety;
Q is H or a protecting group;
L is H or a protecting group;
X is O, S or N;
$R_1$ and $R_1$ are independently H, alkyl, aryl, O-alkyl, O-aryl, carboxylic acid, amide, ester, halogen, trifluoromethyl, or amine;
n is 2–10; and,
Z is H, amine, azide, halogen, thiol, O-alkyl, O-aryl, alkyl, aryl;
comprising the steps of:
providing a compound of the formula V,

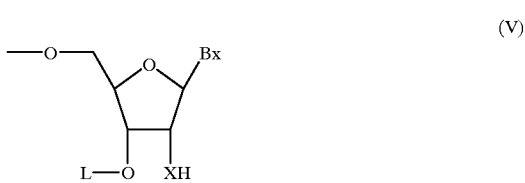

(V)

and treating said compound of the formula V with a compound of formula III

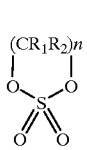

(III)

to give an intermediate compound of formula VI:

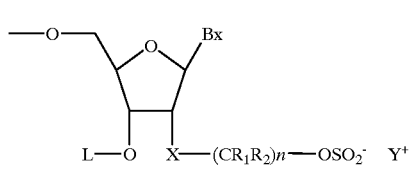

(VI)

wherein:

Y is H, Li, Na, K, Cs or an amine; and, reacting said intermediate compound with a nucleophile, to provide a compound having formula VII.

51. The process of claim 50 wherein said nucleophile is reacted at a temperature of from about 0° C. to about 200° C.

52. The process of claim 50 wherein said nucleophile is reacted over a period of from about 1 hour to about 24 hours.

53. The process of claim 50 wherein said nucleophile is an amine.

54. The process of claim 50 wherein said nucleophile is dimethylamine.

55. The process of claim 50 wherein said nucleophile is an alkoxide.

56. The process of claim 50 wherein said nucleophile is an sodium methoxide.

57. The process of claim 50 wherein said nucleophile is a thiol.

58. The process of claim 50 wherein said nucleophile is a sodium thiomethoxide.

59. A compound of formula VI:

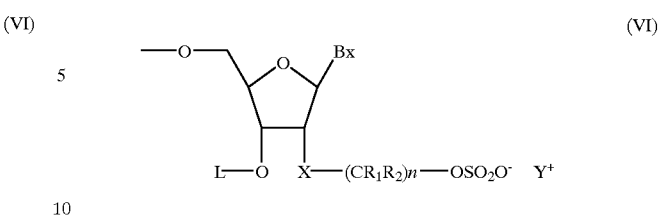

(VI)

wherein:

Bx is a heterocyclic base moiety;

Q is H or a hydroxyl protecting group;

L is H or a hydroxyl protecting group;

X is O, N or S;

$R_1$ and $R_2$ are independently H, alkyl, aryl, O-alkyl, O-aryl, carboxylic acid, amide, ester, halogen, trifluoromethyl, or amine;

n is 2–10;

Y is H,Li,Na,K,Cs or an amine.

60. The compound of claim 59 wherein Bx is a purine or a pyrimidine base optionally substituted with a protecting group.

61. The compound of claim 59 wherein said heterocyclic base moiety is N3-protected-5-methylthymidine, N3-protected-5-methyluridine, N3-protected-uridine, cytidine, 5-methylcytodine, guanosine, adenosine, or 2,6-diaminopurine.

62. The compound of claim 61 wherein said N-3 protecting group is benzyloxymethyl.

* * * * *